United States Patent [19]

Tominaga et al.

[11] Patent Number: 4,585,774
[45] Date of Patent: Apr. 29, 1986

[54] ANILINE DERIVATIVES AND CARDIOTONIC COMPOSITION

[75] Inventors: Michiaki Tominaga; Yung-hsiung Yang; Hidenori Ogawa; Kazuyuki Nakagawa, all of Tokushima, Japan

[73] Assignee: Otsuka Pharmaceutical Co., Ltd., Tokyo, Japan

[21] Appl. No.: 432,902

[22] PCT Filed: May 4, 1982

[86] PCT No.: PCT/JP82/00152
§ 371 Date: Sep. 29, 1982
§ 102(e) Date: Sep. 29, 1982

[87] PCT Pub. No.: WO82/03861
PCT Pub. Date: Nov. 11, 1982

[30] Foreign Application Priority Data

May 8, 1981 [JP] Japan .................. 56-69690
Nov. 6, 1981 [JP] Japan .................. 56-178722

[51] Int. Cl.$^4$ .................. A61K 31/495; C07D 295/10
[52] U.S. Cl. .................. 514/255; 544/121; 544/357; 544/360; 544/372
[58] Field of Search .......... 544/391, 250, 121, 357, 544/360, 372; 424/248.54; 514/255

[56] References Cited

U.S. PATENT DOCUMENTS 3,352,866 11/1967 Dornfeld .................. 544/391
4,223,034 9/1980 Hadley .................. 544/391

FOREIGN PATENT DOCUMENTS 1434323 5/1976 United Kingdom .

OTHER PUBLICATIONS

Otto, "Chemical Abstracts", vol. 82, 1975, col. 43459s.
Munakata, et al., "Chemical Abstracts", vol. 95, 1981, col. 95:115751z.

Primary Examiner—Glennon H. Hollrah
Assistant Examiner—James H. Turnipseed
Attorney, Agent, or Firm—Finnegan, Henderson, Farabow, Garrett & Dunner

[57] ABSTRACT

Aniline derivatives of the formula:

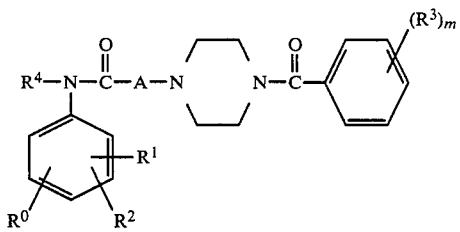

wherein $R^0$, $R^1$ and $R^2$ are the same or different and each is a hydrogen atom, a halogen atom, a nitro group, an amino group, a carboxy group, a cyano group, a hydroxy group, a sulfonamido group, a lower alkyl group, a lower alkoxycarbonyl group, a lower alkoxy group, a lower alkanoyl group, a lower alkylamino group, a lower alkylthio group, a lower alkanoylamino group or a group of the formula

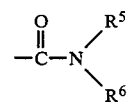

wherein $R^5$ and $R^6$ are the same or different and each is a hydrogen atom, a lower alkyl group or a $C_3$ to $C_8$ cycloalkyl group or together with the nitrogen atom a morpholino, piperidino, piperazino or pyrrolidino group; $R^3$ is a cyano group, a nitro group, a halogen atom, a lower alkyl group or a lower alkoxy group; m is an integer of 1 to 3; $R^4$ is a hydrogen atom or a lower alkyl group; and A is a lower alkylene group. The derivatives are useful as cardiotonics.

13 Claims, No Drawings

ANILINE DERIVATIVES AND CARDIOTONIC COMPOSITION

TECHNICAL FIELD

The present invention relates to novel aniline derivatives and their salts.

DISCLOSURE OF INVENTION

Compounds of the present invention are novel ones which have not been disclosed in any literature, and are represented by the following general formula,

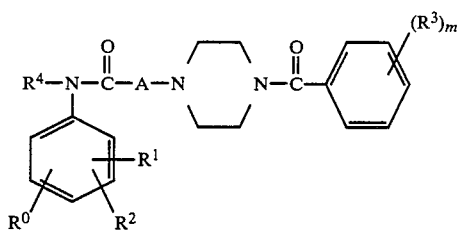

[wherein $R^0$, $R^1$ and $R^2$ are the same or different and each are a hydrogen atom, a halogen atom, a nitro group, an amino group, a carboxy group, a cyano group, a hydroxy group, a sulfonamido group, a lower alkyl group, a lower alkoxycarbonyl group, a lower alkoxy group, a lower alkanoyl group, a lower alkylamino group, a lower alkylthio group, a lower alkanoylamino group or a group of the formula

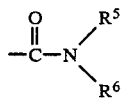

(wherein, $R^5$ and $R^6$ are the same or different and each are a hydrogen atom, a lower alkyl group or a cycloalkyl group; or said $R^5$ and $R^6$ may form 5- or 6-membered saturated heterocyclic group together with the nitrogen atom adjacent thereto, or further with or without a nitrogen atom or oxygen atom); $R^3$ is a cyano group, a nitro group, a halogen atom, a lower alkyl group or a lower alkoxy group; m is an integer of 1 to 3; $R^4$ is a hydrogen atom or a lower alkyl group; A is a lower alkylene group; provided that when $R^3$ is a lower alkoxy group, a halogen atom or a lower alkyl group; and when $R^0$ is a hydrogen atom and further A is a methylene group, then $R^1$ and $R^2$ are the same or different and should not be hydrogen atoms, halogen atoms, lower alkyl groups or lower alkoxy groups; further when $R^3$ is a lower alkoxy group, a halogen atom or a lower alkyl group, and $R^0$ is a halogen atom, a lower alkyl group or a lower alkoxy group and A is a methylene group, then either one of $R^1$ or $R^2$ is a hydrogen atom and the other one should not be a halogen atom, a lower alkyl group or a lower alkoxy group.]

BEST MODE FOR CARRYING OUT THE INVENTION

Aniline derivatives and their salts represented by the general formula (1) are novel drugs and act directly to the heart, and have myocardial contraction increasing activity (positive inotropic activity) and coronary blood flow increasing activity, and thus they are useful as cardiotonics for curing various heart diseases such as acute left venticular heart failure, cardiogenic shock, low output heart failure syndrome and the like. Specifically, aniline derivatives and their salts represented by the general formula (1) of the present invention are characterized as their low toxicities to the heart, thus they have almost no heart beat increasing activity.

As to the lower alkoxycarbonyl group mentioned in the present specification, an alkoxycarbonyl group having 1 to 6 carbon atoms in the alkoxy moiety, such as methoxycarbonyl, ethoxycarbonyl, propoxycarbonyl, isopropoxycarbonyl, butoxycarbonyl, tert-butoxycarbonyl, pentyloxycarbonyl or hexyloxycarbonyl group or the like can be exemplified.

As to the lower alkoxy group mentioned in the present specification, an alkoxy group having 1 to 6 carbon atoms, such as methoxy, ethoxy, propoxy, isopropoxy, butoxy, tert-butoxy, pentyloxy or hexyloxy group or the like can be exemplified.

As to the lower alkylene group mentioned in the present specification, an alkylene group having 1 to 6 carbon atoms, such as methylene, ethylene, trimethylene, 2-methyltrimethylene, tetramethylene, 1-methyltetramethylene, pentamethylene or hexamethylene group or the like can be exemplified.

As to the group of the formula

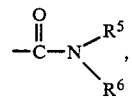

(wherein $R^5$ and $R^6$ are the same or different, and each are a hydrogen atom, a lower alkyl group or a cycloalkyl group), there are exemplified such as carbamoyl, methylaminocarbonyl, ethylaminocarbonyl, propylaminocarbonyl, isopropylaminocarbonyl, butylaminocarbonyl, tert-butylaminocarbonyl, pentylaminocarbonyl, hexylaminocarbonyl, dimethylaminocarbonyl, diethylaminocarbonyl, dipropylaminocarbonyl, diisopropylaminocarbonyl, dibutylaminocarbonyl, di-tert-butylaminocarbonyl, dipentylaminocarbonyl, dihexylaminocarbonyl, methylethylaminocarbonyl, methylpropylaminocarbonyl, methylisopropylaminocarbonyl, methylbutylaminocarbonyl, methyl-tert-butylaminocarbonyl, ethylpropylaminocarbonyl, cyclopropylaminocarbonyl, cyclobutylaminocarbonyl, cyclopentylaminocarbonyl, cyclohexylaminocarbonyl, cycloheptylaminocarbonyl, cyclooctylaminocarbonyl, dicyclopentylaminocarbonyl, dicyclohexylaminocarbonyl, cyclopentylcyclohexylaminocarbonyl, cyclohexylmethylaminocarbonyl, cyclopentylethylaminocarbonyl, cyclohexyl-n-butylaminocarbonyl or cyclooctylmethylaminocarbonyl group or the like.

Further, as to the group of the formula

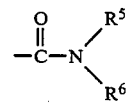

(wherein 5- or 6-membered saturated heterocyclic group formed together with the adjacent nitrogen atom, or further with or without a nitrogen atom or oxygen atom), there are exemplified such as morpholino, piperidino, piperazino or pyrrolidino group or the like.

As to the halogen atom mentioned in the present specification, fluorine atom, chlorine atom, bromine atom or iodine atom are exemplified.

As to the lower alkyl group mentioned in the present specification, an alkyl group having 1 to 6 carbon atoms, such as methyl group, ethyl group, propyl group, isopropyl group, butyl group, tert-butyl group, pentyl group or hexyl group can be exemplified.

As to the lower alkanoylamino group mentioned in the present specification, an alkanoylamino group having 1 to 6 carbon atoms in the alkanoyl moiety, such as formylamino, acetylamino, propionylamino, butyrylamino, isobutylcarbonylamino, tert-butylcarbonylamino, pentanoylamino or hexanoylamino group or the like can be exemplified.

As to the lower alkanoyl group mentioned in the present specification, an alkanoyl group having 1 to 6 carbon atoms, such as formyl, acetyl, propionyl, butyryl, isobutylcarbonyl, tert-butylcarbonyl, pentanoyl or hexanoyl group can be exemplified.

As to the lower alkylamino group mentioned in the present specification, an amino group having one or two alkyl group having 1 to 6 carbon atoms in the alkyl moieties, such as methylamino, ethylamino, propylamino, isopropylamino, butylamino, tert-butylamino, pentylamino, hexylamino, dimethylamino, diethylamino, dipropylamino, diisopropylamino, dibutylamino, di-tert-butylamino, dipentylamino, dihexylamino, methylethylamino, methylpropylamino, methylisopropylamino, methylbutylamino, methyl-tert-butylamino or ethylpropylamino group or the like can be exemplified.

As to the lower alkylthio group mentioned in the present specification, there are exemplified such as methylthio, ethylthio, propylthio, isopropylthio, butylthio, tert-butylthio, pentylthio or hexylthio group or the like.

As to the cycloalkyl group mentioned in the present specification, there are exemplified a cycloalkyl group having 3 to 8 carbon atoms such as cyclopropyl, cyclobutyl, cyclopentyl, cyclohexyl, cycloheptyl or cyclooctyl group or the like.

Aniline derivatives and salts thereof represented by the general formula (1) of the present invention can be prepared by methods of the reaction process formulas as follows:

Reaction process formula - 1

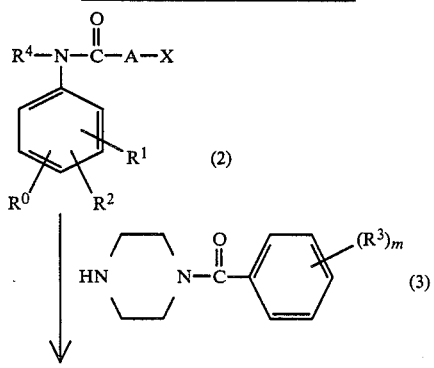

-continued
Reaction process formula - 1

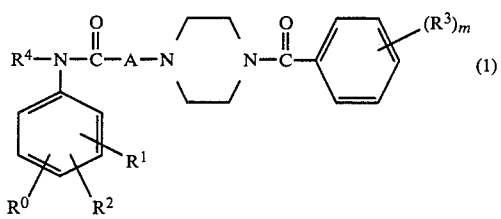

wherein $R^0$, $R^1$, $R^2$, $R^3$, $R^4$, A and m are the same as defined previously; and X is a halogen atom.

Thus, aniline derivatives represented by the general formula (1) of the present invention are prepared by reacting an anilide derivative represented by the general formula (2) with a piperazine derivative represented by the general formula (3).

The above reaction is generally carried out in an inert solvent, at a temperature condition from a room temperature to about 100° C., preferably at a room temperature to 80° C., and is completed for about 1 hour to 24 hours.

As to the inert solvent, an ether for example dioxane, tetrahydrofuran, ethylene glycol dimethyl ether, diethyl ether or the like; an aromatic hydrocarbon for example benzene, toluene, xylene or the like; a lower alcohol for example methanol, ethanol or the like; a polar solvent for example dimethylformamide, dimethyl sulfoxide, hexamethylphosphoric triamide, acetone, acetonitrile or the like can be used.

The above reaction can advantageously be carried out by using a basic compound as a deacidifying agent. As to the basic compound, potassium carbonate, sodium carbonate, sodium hydroxide, sodium hydrogencarbonate, sodium amide, sodium hydride, a tertiary amine such as triethylamine, tripropylamine, pyridine, quinoline or the like can be exemplified.

The above reaction can be carried out, if necessary by adding an alkali metal iodide for example, potassium iodide, sodium iodide or the like, or hexamethylphosphoric triamide as a reaction promoter.

The ratio of the amount of a compound represented by the general formula (2) to the amount of a compound represented by the general formula (3) in the above-mentioned reaction is not specifically restricted, and the ratio can be selected from a wide range, generally an equimolar amount to an excess amount, preferably an equimolar amount to 5 times the moalr quantity, more preferably 1 to 1.2 times the molar quantity of the latter may be used to the former.

A compound of the general formula (2) and a compound of the general formula (3) both of which are used in the reaction process formula-1 can easily be prepared by methods according to reaction process formulas-2 and -3 as follows:

Reaction process formula - 2

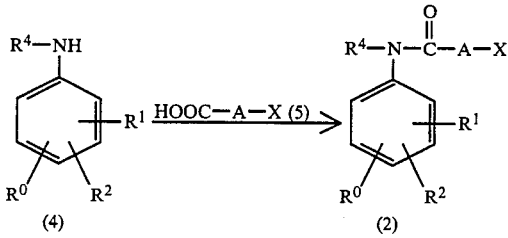

wherein $R^0$, $R^1$, $R^2$, $R^4$, A and X are the same as defined previously.

A compound represented by the general formula (2) is prepared by reacting a known aniline derivative represented by the general formula (4) with a carboxylic acid derivative represented by the general formula (5) under condition of a common amide-bond formation reaction. In this case, a compound having the carboxy group which is being activated can be used in place of a compound of the general formula (5), further a compound having the amino group which is being activated can be used in place of a compound of the general formula (4).

As to the amide-bond formation reaction, a common reaction condition of amide-bond formation reaction can be applied, for example (a) a mixed acid anhydride method, that is a method by reacting a carboxylic acid (5) with an alkylhalocarboxylic acid to obtain a mixed acid anhydride, then reacting said mixed acid anhydride with a compound of the general formula (4); (b) an activated ester method, that is a method by converting a carboxylic acid (5) into an activated ester for example p-nitrophenyl ester, N-hydroxysuccinimide ester, 1-hydroxybenzotriazole ester or the like, then reacting said activated ester with a compound of the general formula (4); (c) a carbodiimide method, that is a method by dehydrocondensing a carboxylic acid (5) with a compound of general formula (4) in the presence of a dehydrating agent such as dicyclohexylcarbodiimide, carbonyldiimidazole or the like; (d) a carboxylic acid halide method, that is a method by converting a carboxylic acid (5) into a carboxylic acid halide, then reacting said halide with a compound of the general formula (4); (e) as to other methods, for example, a method by converting a carboxylic acid (5) into a carboxylic acid anhydride by using for example acetic anhydride as a dehydrating agent, then reacting said carboxylic acid anhydride with a compound of the general formula (4); or a method by reacting an ester of a carboxylic acid (5) of a lower alcohol with a compound of the general formula (4) under a high pressure and at an elevated temperature. Among these methods, the mixed acid anhydride method and carboxylic acid halide method are preferable.

As to the alkylhalocarboxylic acid used in the mixed acid anhydride method, there can be exemplified methyl chloroformate, methyl bromoformate, ethyl chloroformate, ethyl bromoformate, isobutyl chloroformate or the like. The mixed acid anhydride is prepared by a conventional Schotten-Baumann reaction, and said mixed acid anhydride is reacted, without being separated from the reaction system, with a compound of the general formula (4) to obtain a compound of the general formula (2). The Schotten-Bauman reaction is generally carried out in the presence of a basic compound. As to the basic compound, any compound usually used in Schotten-Bauman reaction can also be used, for example an organic base such as triethylamine, trimethylamine, pyridine, dimethylaniline, N-methylmorpholine, 1,5-diazabicyclo-[4,3,0]nonene-5(DBN), 1,5-diazabicyclo-[5,4,0]undecene-5 (DBU), 1,4-diazabicyclo[2,2,2]octane (DABCO) or the like; an inorganic basic compound such as potassium carbonate, sodium carbonate, potassium hydrogencarbonate, sodium hydrogencarbonate or the like can be exemplified. Said reaction is carried out at $-20°$ to $100°$ C., preferably at $0°$ to $50°$ C., and the reaction time is about 5 minutes to 10 hours. The reaction of a mixed acid anhydride thus obtained with a compound of the general formula (4) is carried out at about $-20°$ to $150°$ C., preferably at $10°$ to $50°$ C. for about 5 minutes to 10 hours. The mixed acid anhydride method is generally carried out in a solvent. As to the solvent used in the reaction, any solvent conventionally used in a mixed acid anhydride method can also be used, concretely a halogenated hydrocarbon such as methylene chloride, chloroform, dichloroethane or the like; an aromatic hydrocarbon such as benzene, toluene, xylene or the like; an ether such as diethyl ether, tetrahydrofuran, dimethoxyethane or the like; an ester such as methyl acetate, ethyl acetate or the like; an aprotic polar solvent such as dimethylformamide, dimethyl sulfoxide, hexamethylphosphoric triamide or the like, are exemplified. In carrying out the reaction, the ratio of the amount of a carboxylic acid (5), to the amount of an alkylhalocarboxylic acid and to the amount of a compound of the general formula (4) is not specifically restricted, and generally an equimolar amount each of these reactants are used, and preferably 1 to 1.5 times the molar quantity of the alkylhalocarboxylic acid and of the compound of the general formula (4) may be used to the carboxylic acid (5).

In carrying out the carboxylic acid halide method, the carboxylic acid (5) is reacted with a halogenating agent to obtain a carboxylic acid halide, then said carboxylic acid halide is separated from the reaction system, or is not separated from the reaction system, and reacted with a compound of the general formula (4) to prepare a compound of the general formula (2).

The reaction of a carboxylic acid (5) with a halogenating agent can be carried out in the absence or presence of a solvent. As to the solvent, any solvent which does not give any adverse effect to the reaction can be used, for example an aromatic hydrocarbon such as benzene, toluene, xylene or the like; a halogenated hydrocarbon such as chloroform, methylene chloride, carbon tetrachloride or the like; an ether such as dioxane, tetrahydrofuran, diethyl ether or the like; dimethylformamide or dimethyl sulfoxide can be exemplified. As to the halogenating agent, a common halogenating agent which can convert the hydroxyl group in the carboxy group may be used, for example thionyl chloride, phosphorus oxychloride, phosphorus oxybromide, phosphorus penetachloride, phosphorus pentabrimide or the like may be exemplified. The ratio of the amount of carboxylic acid (5) to the amount of the halogenating agent is not specifically restricted, and can be selected from a wide range. In case that the reaction is carried out in the absence of a solvent, generally the latter is used in an excess amount to the former. While, in case that the reaction is carried out in the presence of a solvent, generally the latter is used at least an equimolar quantity, preferably 2 to 4 times the molar quantity to the former. The reaction temperature (and the reaction time) is not specifically restricted, and generally the reaction is carried out at a room temperature to 100° C., preferably 50° to 80° C. for about 30 minutes to 6 hours.

The reaction of the carboxylic acid halide thus obtained with a compound of the general formula (4) is carried out in the presence of a dehydrohalogenating agent. As to the dehydrohalogenating agent, generally a basic compound is used, for example an inorganic basic compound such as sodium hydroxide, potassium hydroxide, sodium carbonate, potassium carbonate, sodium hydrogencarbonate, potassium hydrogencarbonate, silver carbonate or the like; an alcoholate such as sodium methylate, sodium ethylate or the like; an organic basic compound such as triethylamine, pyridine, N,N-dimethylaniline, N-methylmorpholine, 4-dimethylaminopyridine, 1,5-diazabicyclo[4,3,0]-nonene-5 (DBN), 1,5-diazabicyclo[5,4,0]undecene-5 (DBU), 1,4-diazabicyclo[2,2,2]-octane (DABCO) or the like can be exemplified. On the other hand, by using an excess amount of a compound of the formula (4), it can be served both as the starting material and the dehydrohalogenating agent. Said reaction can be carried out in the absence or presence of a solvent. Any inert solvent which does not give any adverse effect to the reaction can be used, for example a halogenated hydrocarbon such as chloroform, methylene chloride, carbon tetrachloride or the like, an ether such as diether ether, tetrahydrofuran, dioxane or the like, an aromatic hydrocarbon such as benzene, toluene, xylene or the like, an ester such as methyl acetate, ethyl acetate or the like, an aprotic polar solvent such as N,N-dimethylformamide, dimethyl sulfoxide, hexamethylphosphoric triamide can be exemplified. The ratio of the amount of carboxylic acid halide to the amount of a compound of the general formula (4) is not specifically restricted, in case that the reaction is carried out in the presence of a solvent, generally the former is used in an equimolar amount, preferably 1 to 2 times the molar quantity to the latter. The reaction temperature and the reaction time are not specifically restricted, generally the reaction is carried out at −30° to 100° C., preferably at 0° to 50° C., for about 30 minutes to 12 hours.

Reaction process formula - 3

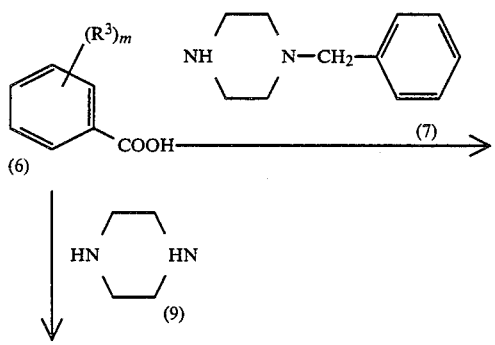

-continued
Reaction process formula - 3

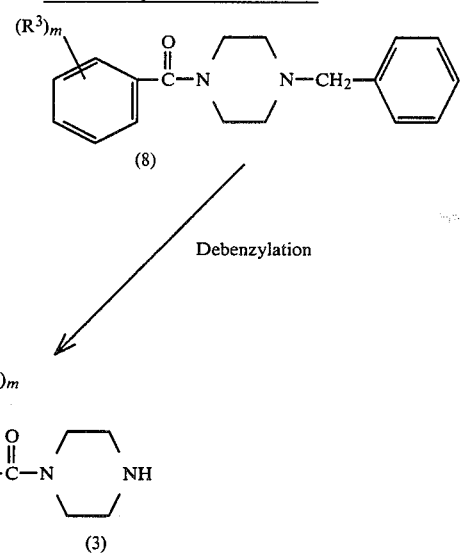

wherein $R^3$ and m are the same as defined previously.

A compound represented by the general formula (3) can be obtained by reacting a compound represented by the general formula (6) with piperazine (9), or by debenzylating a compound represented by the general formula (8) which is obtained by reacting a compound represented by the general formula (6) with N-benzylpiperzine (7).

The reaction of a compound of the general formula (6) with piperazine (9) can be carried out by a reaction condition similar to that of the reaction of a compound of the general formula (4) with a compound of the general formula (5), and about an equimolar quantity of piperazine may be used to a compound of the general formula (6).

The reaction of a compound of the general formula (6) with N-benzylpiperazine (7) can be carried out by a reaction condition similar to that of the reaction of a compound of the general formula (4) with a compound of the general formula (5).

The debenzylation of a compound of the general formula (8) can be carried out under a condition widely selected from the reaction conditions of conventional debenzylation reaction, for example, the debenzylation can be carried out in a suitable solvent, in the presence of a catalyst lfor catalytic reduction, such as palladium-carbon, palladium black, platinum black or the like at 0° C. to a room temperature for 0.5 to 5 hours. As to the solvent, water, a lower alcohol such as methanol, ethanol, isopropanol or the like, an ether such as dioxane, tetrahydrofuran or the like, or acetic acid can be exemplified. The catalyst for catalytic reduction can generally be used in about 10 to 50% by weight to the amount of a compound of the general formula (8). Further, an acid such as a concentrated hydrochloric acid may be added into the reaction system for accelarating the reaction.

Further, the compound of the present invention can be prepared by a method as shown in the Reaction process formula-4 below:

Reaction process formula - 4

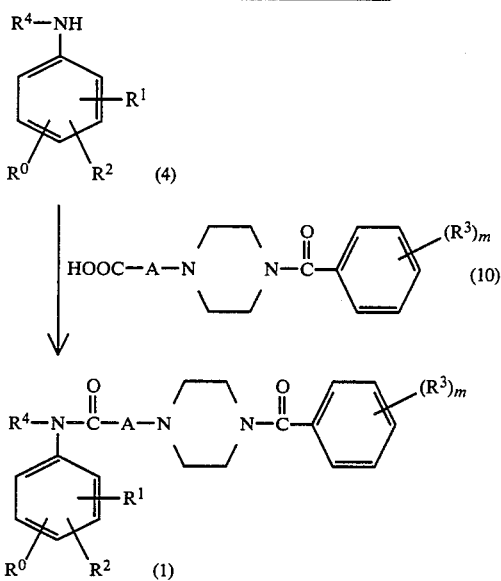

wherein $R^0$, $R^1$, $R^2$, $R^3$, $R^4$, A and m are the same as defined previously.

The reaction of a compound of the general formula (4) with a compound of the general formula (10) can be carried out by a reaction condition similar to that of the reaction of the reaction of a compound of the general formula (4) with a compound of the general formula (5).

A compound of the general formula (10) used in Reaction process formula-4 can be prepared by a method for example of the following Reaction process formula-5 or -6.

Reaction process formula - 5

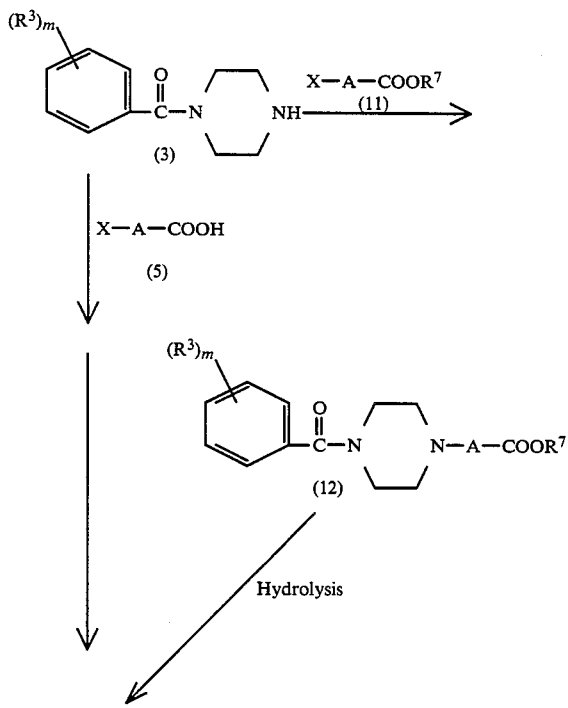

-continued
Reaction process formula - 5

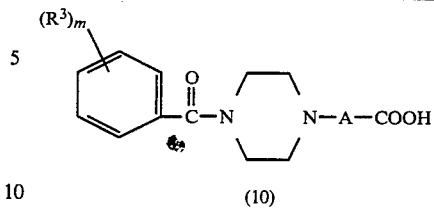

wherein $R^3$, A, m and X are the same as defined previously, and $R^7$ is a lower alkyl group.

The reaction of a compound of the general formula (3) with a compound of the general formula (5) can be carried out by a reaction condition similar to that of the reaction of the reaction of a compound of the general formula (2) with a compound of the general formula (3), and the basic compound as the deacidifying agent may be used at least 2 times the molar quantity, preferably 2 to 4 times the molar quantity to the amount of a compound of the general formula (5).

The reaction of a compound of the general formula (3) with a compound of the general formula (11) can be carried out by a reaction condition similar to that of the reaction condition of a compound of the general formula (2) with a compound of the general formula (3).

The hydrolysis of a compound of the general formula (12) is generally carried out in the presence of a catalyst, and any catalyst for common hydrolysis reaction can be used, as to a typical catalyst, a basic compound such as sodium hydroxide, potassium hydroxide, barium hydroxide or the like, or a mineral acid such as sulfuric acid, hydrochloric acid, nitric acid or the like can be exemplified. The amount of the catalyst is not specifically restricted and may suitably be selected from a wide range. The hydrolysis may be carried out by a conventional procedure, and generally it is carried out advantageously in the presence of a solvent, and any solvent which does not give any adverse effect to the reaction can be used, for example water, a lower alcohol such as methanol, ethanol, isopropanol or the like can be exemplified. The reaction temperature is not specifically restricted and can be suitably selected from a wide range, and generally the reaction can be carried out at a room temperature to about 150° C., preferably, 50° to 110° C. The reaction is generally completed in 30 minutes to 10 hours.

Reaction process formula - 6

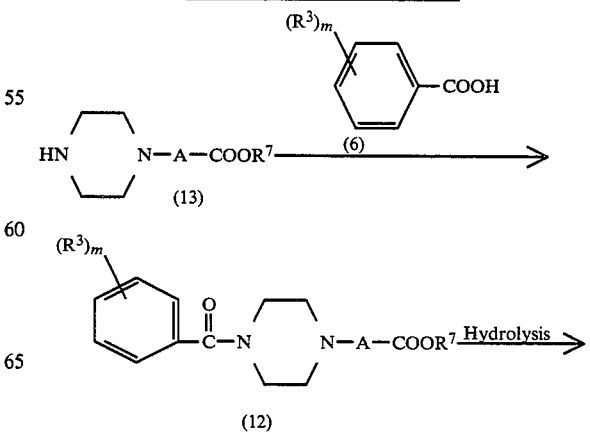

-continued
Reaction process formula - 6

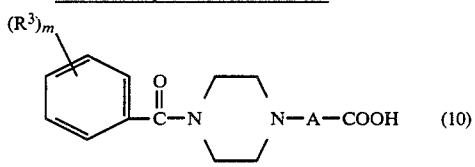

wherein $R^3$, A, m and $R^7$ are the same as defined previously.

The reaction of a compound represented by the general formula (13) with a carboxylic acid derivative of the general formula (6) can be carried out under a condition similar to the condition of the reaction of a compound of the general formula (4) with a carboxylic acid derivative of the general formula (5). The hydrolysis of a compound of the general formula (12) can be carried out as explained in the above-mentioned Reaction process formula-5.

A compound represented by the general formula (1) of the present invention can also be prepared by a method of Reaction process formula-7 as follows:

Reaction process formula-7

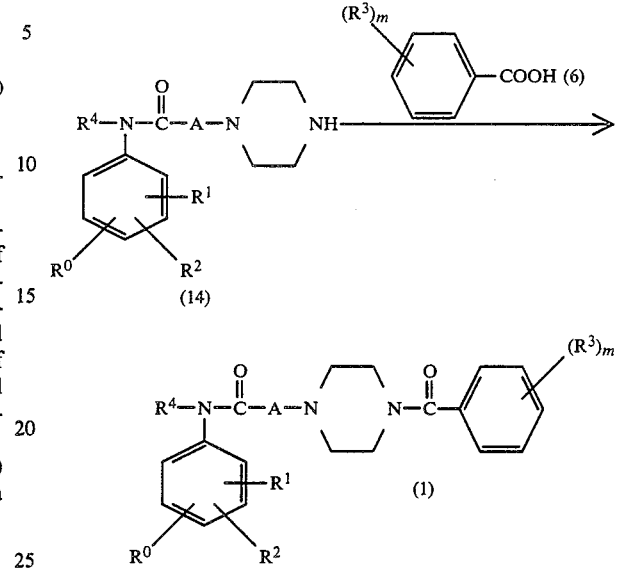

wherein $R^0$, $R^1$, $R^2$, $R^3$, $R^4$, A and m are the same as defined above.

The reaction of a compound represented by the general formula (14) with a compound of the general formula (6) can be carried out under a condition similar to the condition of the reaction of a compound of the general formula (4) with a compound of the general formula (5).

A compound of the general formula (14) used in Reaction process formula-7 can be prepared by a method for example of the following Reaction process formula-8.

Reaction process formula-8

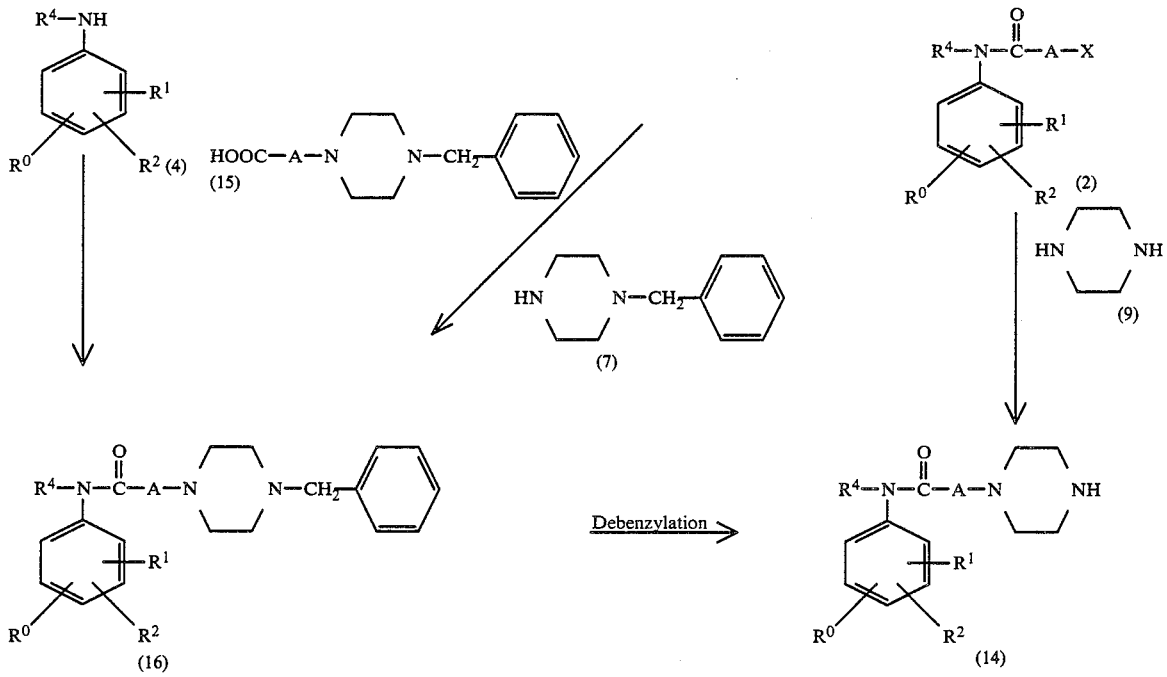

wherein $R^0$, $R^1$, $R^2$, $R^4$, A and X are the same as defined previously.

The reaction of a compound of the general formula (4) with a compound of the general formula (15) can be carried out under a condition similar to the condition of the reaction of a compound of the general formula (4) with a compound of the general formula (5).

Further, the reaction of a compound of the general formula (2) with N-benzylpiperazine (7) can be carried out under a condition similar to the condition of the reaction of a compound of the general formula (2) with a compound of the general formula (3).

The debenzylation of a compound of the general formula (16) can be carried out under a condition similar to the debenzylation of a compound of the general formula (8).

Among compounds represented by the general formula (1), a compound in which $R^4$ is a lower alkyl group [the general formula (1b)] can be prepared by reacting a compound in which $R^4$ is a hydrogen atom [the general formula (1a)] with a compound of the general formula (17), as shown in Reaction process formula-9 as follows:

Reaction process formula-9

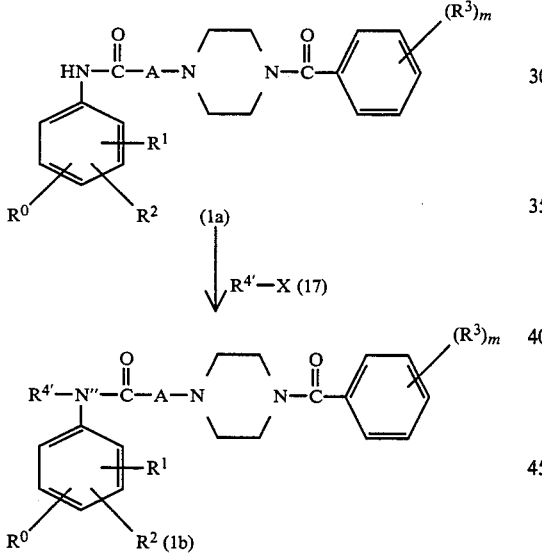

wherein $R^0$, $R^1$, $R^2$, $R^3$, A, m and X are the same as defined previously, and $R^{4'}$ is a lower alkyl group.

The alkylation reaction of a compound of the general formula (1a) is carried out in a suitable solvent, in the presence of a basic compound by reacting with a compound of the general formula (17). As to the solvent, any one which does not give anyl adverse effect to the reaction can be used, for example a halogenated hydrocarbon such as chloroform, methylene chloride, carbon tetrachloride or the like, an aromatic hydrocarbon such as toluene, xylene or the like, an ester such as methyl acetate, ethyl acetate or the like, an aprotic polar solvent such as N,N-dimethylformamide, dimethyl sulfoxide, hexamethylphosphoric triamide or the like, an ether such as dioxane, diethylene glycol dimethyl ether, diethyl ether or the like can be exemplified. As to the basic compound, sodium hydride, potassium metal, sodium metal, sodium amide, potassium amide or the like can be exemplified.

The ratio of the amount of a compound of the general formula (1a) to the amount of a compound of the general formula (17) is not specifically restricted and it is suitably selected from a wide range, generally at least an equimolar quantity, preferably an equimolar to about 2 times the molar quantity of the latter can be used to the former. The reaction temperature is generally 0° to 70° C., preferably 0° to a room temperature. The reaction is generally completed in 0.5 to 12 hours.

Among a compound represented by the general formula (1), a compound in which any two of the substituted groups among of $R^0$, $R^1$ and $R^2$ are hydrogen atoms and the remaining one is a carboxyl group can be converted into an ester of an amide compound [general formula (1d)] by a method as shown in the following Reaction process formula-10. Alternatively, a compound of the general formula (1d) can be converted into a compound of the general formula (1c).

Reaction process formula-10

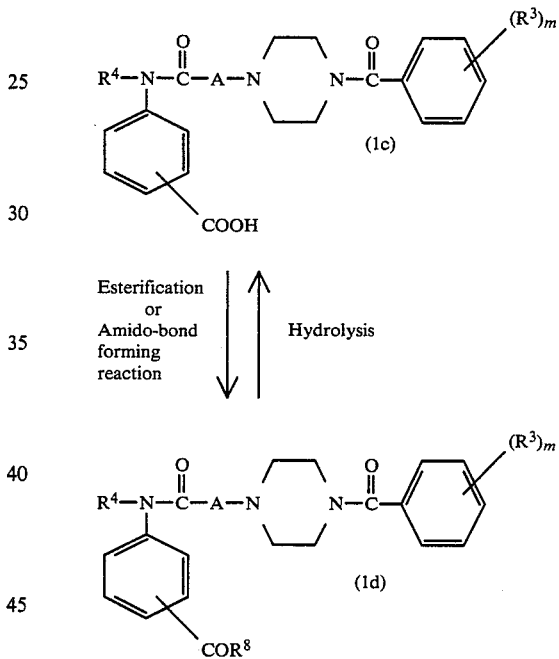

wherein $R^3$, $R^4$, A and m are the same as defined previously; $R^8$ is a lower alkyl group or group of the formula

(wherein $R^5$ and $R^6$ are the same as defined previously).

The esterification of a compound of the general formula (1c) can be carried out by a method of conventional esterification reaction, for example (a) a method by reacting a compound of the general formula (1c) with a lower alcohol in an excess amount in the presence of a mineral acid such as sulfuric acid, hydrochloric acid or the like, or boron trifluoride as the catalyst; (b) a method by reacting a compound of the general formula (1c) with an alkylating agent such as diazomethane, a dialkyl sulfate, can be exemplified.

The amino-bond formation reaction of a compound of the general formula (1c) with

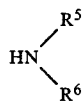

can be carried out under the condition similar to the reaction condition of compounds of (4) with (5). Further, the hydrolysis of a compound of the general formula (1d) can be carried out under the hydrolysis of a compound of the general formula (12).

Among compounds represented by the general formula (1) of the present invention, a compound having amino group(s) as the substituent(s) on the phenyl ring can be prepared by reducing a compound having nitro group(s) as the substituent(s) on the phenyl ring. This reduction reaction can be carried out under a condition generally used in reducing an aromatic nitro group to the corresponding aromatic amino group, more specifically a method by using a metal such as iron or zinc, or stannous chloride with a mineral acid such as hydrochloric acid or sulfuric acid, or a method by using sodium sulfite, sulfur dioxide gas as the reducing agent, or a method of catalytic reduction by using palladium-carbon or the like as the catalyst.

Aniline derivatives of the present invention thus obtained can easily be converted into their acid addition salt by reaction with pharmaceutically acceptable acids. The present invention includes such acid addition salts. The examples of such acids including inorganic acids such as hydrochloric acid, sulfuric acid, phosphoric acid, hydrobromic acid or the like; organic acids such as acetic acid, oxalic acid, succinic acid, maleic acid, fumaric acid, malic acid, tartaric acid, citric acid, malonic acid, methanesulfonic acid, benzoic acid or the like.

Among the aniline derivative represented by the general formula (1) of the present invention, those having acidic group can easily be converted into pharmacologically acceptable salts by reacting basic compounds. The examples of such basic compounds including sodium hydroxide, potassium hydroxide, calcium hydroxide, sodium carbonate, potassium hydrogencarbonate or the like.

The objective compounds as prepared by the procedures in the above-mentioned various reaction process formulas can easily be isolated and purified by conventional separation means such as solvent extraction method, dilution method, distillation method, recrystallization method, column chromatography, preparative thin-layer chromatography or the like.

Aniline derivatives of the present invention also including their optical isomers.

Aniline derivatives of the general formula can be used in the form of pharmaceutical composition generally used in the art. Such pharmaceutical composition can be prepared by using diluents or excipients such as fillers, diluents, binders, wetting agents, disintegrators, surface active agents, lublicants. The pharmaceutical compositions can be selected in any desired unit form, including tablets, pills, powder, liquors, suspensions, emulsions, granules, capsules, suppositories, injections (solutions and suspensions). For the purpose of to shape in the form of tablets, carriers which are known in this field can be used, for example, excipients such as lactose, sucrose, sodium chloride, glucose, urea, starch, calcium carbonate, caolin, crystallin cellulose, or silicic acid or the like; binding agents such as water, ethanol, propanol, simple syrup, a solution of glucose, a solution of starch, a gelatin solution, carboxymethylcellulose, shelac, methylcellulose, calcium phosphate or polyvinylpyrrolidone or the like; desintegrators such as dried starch, sodium alginate, agar-agar powder, laminalia powder, sodium hydrogen-carbonate, calcium carbonate, poldyoxyethylene sorbitan fatty acid ester, sodium laurylsulfate, monoglyceride of stearic acid, starch, lactose or the like; desintegration inhibitors such as sucrose, stearin, coconut butter, a hydrogenated oil or the like; adsorption accelerators such as a quaternary ammonium base, sodium laurylsulfate or the like; wetting agents such as glycerin, starch or the like; adsorbing agent such as starch, lactose, caoline, bentonite, colloidal silicic acid or the like; lubricants such as purified talc, stearic acid salt, boric acid powder, polyethylene glycol or the like. In case of preparing tablets, they can be further coated with an usual coating material to make sugar coated tablets, gelatin film coated tablets, tablets coated with enteric coatings, tablets coated with films or double-layered tablets and multi-layered tablets. For the purpose of to shape in the form of pills, carriers which are known and used widely in this field can also be used, for example, excipients such as glucose, lactose, starch, coconut butter, hydrogenated vegetable oil, caolin, talc or the like; binders such as powdered gum arabi, powdered tragacanth gum, geletin, ethanol or the like; desintegrators such as laminaria, agar-agar or the like are included.

For the purpose of to shape in the form of supositories, carriers which are known and used widely in this field can also be used, for example, polyethylene glycols, coconut butter higher alcohols, esters of higher alcohols, geletin, semisynthesized glycerides or the like are included.

For the purpose of to make in the form of injection preparation, solutions and suspensions are sterilized and are preferably isotonic to the blood. In making injection preparations, every carriers which are commonly used in this field can also be used, for example, water, ethyl alcohol, propylene glycol, ethoxylated isostearyl alcohol, polyoxylated isostearyl alcohol, polyoxyethylene sorbitan fatty acid esters are included. In these instances, adequate amounts of sodium chloride, glucose or glycerin can be addes to contain in the desired cardiotonic preparations for the purpose of to have them isotonic. Furthermore, the usual dissolving agents, buffer solutions, analgesic agents can be added, as well as coloring agents perfumes, preservatives, seasoning agents, sweetening agents and other medicaments can also be added into the desired preparation, if necessary.

The amount of a compound of the general formula (1) to be contained in the cardiotonic preparations of the present invention is not specifically restricted and it can suitably be selected from a wide range, and generally 1 to 70% by weight, preferably 1 to 30% by weight of the whole composition.

The cardiotonic composition of the present invention can be administered in various forms depending on the purpose without any restriction, thus the cardiotonic composition is administered in a suitable method according to the forms of the preparation, the age of the patiant, the distinction of sex, the conditions of the symptoms and other factors. For example, tablets, pills, solutions, suspensions, emulsions, granules, and capsules are administered orally; and injection preparations are administered intraveneously singly or mixed with injection transfusions such as glucose solutions and amino acids solutions; if necessary the injection preparations are administered singly intramuscularly, intracutaneously, subcutaneously or intraperitoneally; suppositories are administered into rectum.

The administration dosage of a cardiotonic composition of the present invention is suitably selected according to the usage, the age of the patiant, the distinction of sex, the condition of the symptoms and other factors, generally 0.01 to 10 mg/kg, preferably 0.1 to 10 mg/kg of the body weight per day of a compound of the general formula (1) as the active ingredient may be administered, and 0.1 to 200 mg, preferably 1 to 200 mg of the active ingredient may be contained in the administration unit form.

Pharmacological activities of compounds of the general formula (1) of the present invention were conducted by test methods as explained below with the following results.

Compounds used in the tests were as follows:

| Compound No. | Name of the compound |
|---|---|
| 1 | o-Methoxycarbonyl-α-[4-(3,4-dimethoxybenzoyl)-1-piperazinyl]acetanilide |
| 2 | m-Methoxycarbonyl-α-[4-(3,4-dimethoxybenzoyl)-1-piperazinyl]acetanilide monohydrochloride |
| 3 | p-Methoxycarbonyl-α-[4-(3,4-dimethoxybenzoyl)-1-piperazinyl]acetanilide monohydrochloride |
| 4 | o-Carboxy-α-[4-(3,4-dimethoxybenzoyl)-1-piperazinyl]acetanilide monohydrochloride |
| 5 | o-Carbamoyl-α-[4-(3,4-dimethoxybenzoyl)-1-piperazinyl]acetanilide monohydrochloride monohydrate |
| 6 | o-Methoxycarbonyl-N—methyl-α-[4-(3,4-dimethoxybenzoyl)-1-piperazinyl]acetanilide dioxalate |
| 7 | o-Morpholinocarbonyl-α-[4-(3,4-dimethoxybenzoyl)-1-piperazinyl]acetanilide monohydrochloride |
| 8 | o-Nitro-α-[4-(3,4-dimethoxybenzoyl)-1-piperazinyl]acetanilide monohydrochloride |
| 9 | o-Amino-α-[4-(3,4-dimethoxybenzoyl)-1-piperazinyl]acetanilide dihydrochloride semihydrate |
| 10 | 3,4,5-Trimethoxy-α-[4-(3,4-dimethoxybenzoyl)-1-piperazinyl]acetanilide monohydrochloride |
| 11 | o-Acetamido-α-[4-(3,4-dimethoxybenzoyl)-1-piperazinyl]acetanilide monooxalate |
| 12 | o-Acetyl-α-[4-(3,4-dimethoxybenzoyl)-1-piperazinyl]acetanilide |
| 13 | o-Cyano-α-[4-(3,4-dimethoxybenzoyl)-1-piperazinyl]acetanilide monooxalate |
| 14 | p-Dimethylamino-α-[4-(3,4-dimethoxybenzoyl)-1-piperazinyl]acetanilide dihydrochloride dihydrate |
| 15 | m-Methylthio-α-[4-(3,4-dimethoxybenzoyl)-1-piperazinyl]acetanilide monohydrochloride |
| 16 | p-sulfonamido-α-[4-(3,4-dimethoxybenzoyl)-1-piperazinyl]acetanilide monohydrochloride |
| 17 | o-Hydroxy-α-[4-(3,4-dimethoxybenzoyl)-1-piperazinyl]acetanilide monohydrochloride |
| 18 | o-Cyclohexylaminocarbonyl-α-[4-(3,4-dimethoxybenzoyl)-1-piperazinyl]acetanilide |
| 19 | m-Carbamoyl-α-[4-(3,4-dimethoxybenzoyl)-1-piperazinyl]acetanilide monooxalate |
| 20 | o-Carbamoyl-α-[4-(4-nitrobenzoyl)-1-piperazinyl]-acetanilide |
| 21 | p-Carbamoyl-α-[4-(3,4-dimethoxybenzoyl)-1-piperazinyl]acetanilide monohydrochloride monohydrate |
| 22 | o-Hydroxy-m-nitro-α-[4-(3,4-dimethoxybenzoyl)-1-piperazinyl]acetanilide monohydrochloride ¾-hydrate |
| 23 | o-Carbamoyl-α-[4-(3,4-dimethoxybenzoyl)-1-piperazinyl]butyroanilide monooxalate |
| 24 | o-Carbamoyl-γ-[4-(3,4-dimethoxybenzoyl)-1-piperazinyl]butyroanilide monooxalate |
| 25 | o-Carbamoyl-ε-[4-(3,4-dimethoxybenzoyl)-1-piperazinyl]caproanilide monooxalate |
| 26 | o-n-Butylaminocarbonyl-α-[4-(3,4-dimethoxybenzoyl)-1-piperazinyl]acetanilide monooxalate |
| 27 | o-Carbamoyl-α-[4-(3,4,5-trimethoxybenzoyl)-1-piperazinyl]acetanilide |
| 28 | o-Carbamoyl-α-[4-(4-methylbenzoyl)-1-piperazinyl]acetanilide |
| 29 | o-Carbamoyl-α-[4-(4-cyanobenzoyl)-1-piperazinyl]-acetanilide |
| 30 | o-Carbamoyl-α-[4-(3-chlorobenzoyl)-1-piperazinyl]-acetanilide monohydrochloride sesquihydrate |
| 31 | Amrinone: [3-Amino-5-(4-pyridinyl)-2(H)—pyridinone] (Reference compound) |

Pharmacological test—1

Adult mongrel dogs of either sex, weighing 8–13 kg, were anesthetized with sodium petobarbital at a rate of 30 mg/kg by intraveneous administration. After another intraveneous administration of sodium heparin at a rate of 1,000 U/kg, the test dog was sacrificed by blood letting. The heart of the dog was exercised and immediately plunged into Lock's solution, then the right coronary artery was cannulated to the atrinector artery and the right atrium was carefully isolated.

Next, the donor adult mongrel dogs of either sex, weighing 18–27 kg, were anesthetized with sodium pentobarbital at a rate of 30 mg/kg by intraveneous administration, and further treated with intraveneous administration of sodium heparin at a rate of 1,000 U/kg.

The above-mentioned right atrium perfused with the blood conducted from the carotid artery of the donor dog by aid of Peristaric pump. The perfusion pressure was maintained at 100 mm-Hg constantly. The movement of the right atrium was measured through a force-displacement transducer under a static tension of 2 g. The amount of blood flown in the coronary arteries was measured by electromagnetic flow meter. The all data were recorded on an ink-writing recorder. [The method of this test was reported in an article written by Chiba et al., "Japan, Journal of Pharmacology, 25, 433–439, (1975), Naunyn-Schmiedebergs Arch. Pharmakol. Exp. Pathol., 289, 315–325, (1975).]

A solution containing a compound to be tested was injected into the artery through the rubber tube connected close to the cannula, in an amount of 10–30 microliters.

Positive inotropic effect of the compound to be tested is expressed as a percentage of the developed tension before and after the injection of the compound. The effect of the compound on blood flow in coronary artery is expressed as an absolute value (ml/minute) measured from before the injection of the compound. The results are shown in Table 1 below.

TABLE 1

| Compound No. | Dosage | Change of atrial muscle contraction (%) | Change of blood flow in coronary artery |
|---|---|---|---|
| 1 | 1 μ mol | 75.0% | 0.8 ml/minute |
| 2 | 1 μ mol | 57.9% | 3.0 ml/minute |
| 3 | 1 μ mol | 83.8% | 1.5 ml/minute |
| 4 | 1 μ mol | 20.0% | 1.0 ml/minute |

TABLE 1-continued

| Compound No. | Dosage | Change of atrial muscle contraction (%) | Change of blood flow in coronary artery |
| --- | --- | --- | --- |
| 5 | 100 n mol | 120.0% | 0.5 ml/minute |
| 6 | 1 μ mol | 50.0% | 3.5 ml/minute |
| 31 | 1 μ mol | 58.8% | — |

Pharmacological test—2

Adult mongrel dogs of either sex, weighing 8–13 kg, were anesthetized with sodium pentobarbital at a rate of 30 mg/kg by intraveneous administration. After another intraveneous administration of sodium heparin at a rate of 1,000 U/kg, the test dog was sacrificed by blood letting. The heart of the dog was excised, and the preparation was essentially consisting of the anterior papillary muscle and the venticular septum. The preparation was perfused through the cannulated anterior septal artery with the blood from the donor dog at a constant pressure of 100 mm-Hg. The dogs used as the donors were weighing 18–27 kg, and were anesthetized with pentobarbital sodium at a rate of 30 mg/kg by intraveneous administration, and further treated with intraveneous administration of sodium heparin at a rate of 1,000 U/kg. The papilary muscle was driven with rectangular pulse about 1.5-fold the threshold voltage (0.5–3 volts) and 5 seconds duration at a fixed rate of 120 beats/minute through bipolar pacing electrodes. Tension developed by the papillary muscle was measured by strain-gauge transducer. The muscle was loaded with a weight of about 1.5 g. Blood flow through the anterior septal artery was measured by an electromagnetic flow meter. Data of developed tension and blood flow were recorded on charts with an ink-writing rectigraph. [The details of this test method is reported in an article written by Endoh and Hashimoto, "American Journal of Physiology, 218, 1459–1463, (1970)".

A compound to be tested was injected into the intra-arterially in an amount of 10–30 μl in 4 seconds.

The inotropic effects of the compound are expressed as a percentage of the developed tension before the injection of the compound.

The effect of the compound on blood flow are expressed as a difference (ml/minute) of the values before and after the injection of the compound. The results are shown in Table 2 below.

TABLE 2

| Compound No. | Dosage | Change of atrial muscle contraction | Change of blood flow in coronary artery |
| --- | --- | --- | --- |
| 1 | 1 μ mol | 31.8% | 2.0 ml/minute |
| 7 | 1 μ mol | 20.7% | 2.0 ml/minute |
| 8 | 1 μ mol | 80.6% | 2.5 ml/minute |
| 9 | 1 μ mol | 16.7% | 0.5 ml/minute |
| 10 | 1 μ mol | 43.6% | 2.0 ml/minute |
| 11 | 1 μ mol | 22.2% | 1.5 ml/minute |
| 12 | 1 μ mol | 23.5% | 4.5 ml/minute |
| 13 | 1 μ mol | 31.2% | 5.0 ml/minute |
| 14 | 1 μ mol | 21.4% | 3.5 ml/minute |
| 15 | 1 μ mol | 16.7% | 1.5 ml/minute |
| 16 | 1 μ mol | 14.0% | — |
| 17 | 1 μ mol | 33.3% | 3.5 ml/minute |
| 18 | 100 n mol | 10.3% | 1.0 ml/minute |
| 19 | 1 μ mol | 16.7% | 1.0 ml/minute |
| 20 | 1 μ mol | 12.0% | 0.5 ml/minute |
| 21 | 1 μ mol | 16.0% | — |
| 22 | 1 μ mol | 18.0% | — |
| 23 | 1 μ mol | 31.0% | 3.0 ml/minute |

TABLE 2-continued

| Compound No. | Dosage | Change of atrial muscle contraction | Change of blood flow in coronary artery |
| --- | --- | --- | --- |
| 24 | 1 μ mol | 17.9% | 1.0 ml/minute |
| 25 | 1 μ mol | 34.6% | — |
| 26 | 1 μ mol | 17.4% | — |
| 27 | 1 μ mol | 10.0% | — |
| 28 | 1 μ mol | 13.3% | 2.0 ml/minute |
| 29 | 1 μ mol | 19.0% | — |
| 30 | 1 μ mol | 17.7% | — |
| 31 | 1 μ mol | 31.8% | — |

Pharmacological test—3

Mongrel dogs of either sex, weighing 9–15 kg, were anesthetized with sodium pentobarbital initially in a dosage of 30 mg/kg intraveneously and subsequently at a rate of 4 mg/kg/hr intraveneously by using an infusion pump. The animals were respired with room air in a tidal volume of 20 ml/kg at a rate of 18 beats/minutes by using respirator. The chest was opened by a midline incision and the heart was suspended in the pericardial cradle.

The contractile force of the myocardium was measured by means of a Walton-Brodie type strain-gauge arch sutured onto the left ventricle. Systemic blood pressure was measured from the left femoral artery by a pressure transducer. The all data were recorded on charts by use of a rectilinear recorder.

A compound to be tested was injected into the left femoral vein.

The inotropic effects of the compounds are expressed as a percentage of the developed tension before the injection of the compound.

The effect of the compound on blood pressure (mm-Hg) is expressed as a difference between the values before and after the injection of the compound. The results are shown in Table 3 below.

TABLE 3

| Compound No. | Dosage (mg/kg) | Change of contraction of left ventricle (%) | Blood pressure (mm-Hg) | |
| --- | --- | --- | --- | --- |
| | | | Diostasis | Systole |
| 1 | 1 | 43 | −28 | −10 |
| 5 | 1 | 10.9 | −8 | −8 |
| 8 | 1 | 52.2 | −32 | −34 |
| 13 | 1 | 72.2 | −32 | −28 |
| Dobutamine (Reference compound) | 0.01 | 78 | −36 | 28 |

The present invention will be illustrated more specifically by way of the following examples, in which preparation of the compounds to be used as the starting materials will be shown in Reference Examples, and preparation of the objective compounds will be shown in Examples.

REFERENCE EXAMPLE 1

38 Grams of methyl anthranilate and 35 g of potassium carbonate were dissolved in 300 ml of a mixture of acetone-water (2:1), then to this solution was added dropwise 30 g of chloroacetyl chloride under an ice-cooled condition with stirring. After completion of the addition, the reaction was carried out at a room temperature for 2 hours, then 200 ml of water was added to the reaction mixture, and the mixture obtained was ice-cooled, and the crystals precipitated were collected by filtration. The crystals collected were washed with water and ethanol, and recrystallized from methanol to obtain 48.6 g of methyl o-(α-chloroacetylamino)benzoate in the form of colorless needle-like crystals. Melting point: 97°–99° C.

By a method similar to the above, there were obtained compounds as follows:

α-Chloroacetoanilide
  Colorless flake-like crystals (from isopropanol)
  Melting point: 135°–136° C.
Methyl m-(α-chloroacetylamino)benzoate
  Melting point: 92.5°–95° C.
Methyl p-(α-chloroacetylamino)benzoate
  Melting point: 137.5°–141.0° C.

REFERENCE EXAMPLE 2

4.3 Grams of piperazine was added to 50 ml of ethanol, to this solution was added 2.3 g of methyl o-(α-chloroacetylamino)benzoate at a temperature of 40°–50° C. with stirring. The reaction mixture was stirred at the same temperature for 3 hours, then the reaction mixture was concentrated, to the obtained residue was added 20 ml of water, then saturated with sodium chloride, and extracted with chloroform. The chloroform layer was washed with a 10%-sodium hydroxide solution, then washed with a small amount of water and dried. After removal of the solvent by distillation, the residue obtained was purified by a silica gel column chromatography, and recrystallized from ether to obtain 2 g of o-methoxycarbonyl-α-(1-piperazinyl)-acetanilide in the form of colorless needle-like crystals. Melting point: 94°–96° C.

Similarly, by using α-chloroacetanilide in place of methyl o-(α-chloroacetylamino)benzoate, there is obtained α-(1-piperazinyl)acetanilide in the form of colorless amorphous crystals (from tetrahydrofuran-n-hexane). Melting point: 71°–72° C.

Similarly, by using o-carbamoyl-α-chloroacetanilide in place of methyl o-(α-chloroacetylamino)benzoate, there is obtained o-carbamoyl-α-(1-piperazinyl)acetanilide dihydrochloride in the form of colorless cotton fiber-like crystals (from water-acetone). Melting point: 239.5°–242.0° C. (decomposed).

Reference Example 3

25 Grams of methyl o-methylaminobenzoate was dissolved in 125 ml of acetone, to this solution was added a solution prepared by dissolving 20.92 g of potassium carbonate in 60 ml of water. Under an ice-cooled condition, 17.95 g of chloroacetyl chloride was added dropwise thereto, then the reaction mixture was stired at a room temperature for 1 hour. Acetone was removed by distillation, the residue obtained was extracted with chloroform, then the chloroform layer was washed with water, dried and the solvent was removed by distillation. The residue thus obtained was purified by a silica gel column chromatography to obtain 16.80 g of N-methyl-o-methoxycarbonyl-α-chloroacetanilide in the form of colorless oily substance.

NMR(CDCl$_3$)ε: 3.21 (s, 3H), 3.73 (s, 2H), 3.87 (s, 3H), 7.23–7.73 (m, 3H), 7.98 (d-d, J=8 and 2 Hz)

By a method similar to the above, there were obtained compounds as follows:

o-Carbamoly-α-chloroacetanilide
  Colorless needle-like crystals (from ethanol)
  Melting point: 187.5°–189.0° C.
o-Nitro-α-chloroacetanilide
  Light yellow flake-like crystals (from isopropyl ether)
  Melting point: 85.5°–87.0° C.
p-Dimethylamino-α-chloroacetanilide
  Colorless needle-like crystals (from ethanol)
  Melting point: 141°–142° C.
o-Acetyl-α-chloroacetanilide
  Colorless needle-like crystals (from isopropyl ether)
  Melting point: 78°–80.5° C.
m-Methylthio-α-chloroacetanilide
  Colorless needle-like crystals (from 70% water-containing methanol)
  Melting point: 105.5°–107.0° C.
o-Hydroxy-α-chloroacetanilide
  Colorless flake-like crystals (from 50% water-containing methanol)
  Melting point: B 140.5°–141.5° C.
o-Cyano-α-chloroacetanilide
  Colorless needle-like crystals (from 50% water-containing methanol)
  Melting point: 117.0–119.0° C.
p-Sulfonamido-α-chloroacetanilide
  Colorless needle-like crystals (from methanol)
  Melting point: 220.0°–221.0° C.
m-Carbamoyl-α-chloroacetanilide
  Colorless needle-like crystals (from methanol)
  Melting point: 208.0°–209.5° C. (decomposed).
p-Carbamoyl-α-chloroacetanilide
  Colorless needle-like crystals (from 75% water-containing methanol)
  Melting point: 231.0°–233.0° C. (decomposed).
o-Hydroxyl-m-nitro-α-chloroacetanilide
  Light yellow needle-like crystals (from methanol)
  Melting point: 243.0–245.5° C. (decomposed)
o-Carbamoyl-α-bromobutyroanilide
  Colorless needle-like crystals (from methanol-water)
  Melting point: 143.5°–145.5° C.
o-Carbamoyl-γ-chlorobutyroanilide
  Colorless needle-like crystals (from methanol-water)
  Melting point: 112.5°–114.0° C.
o-Carbamoyl-ε-bromocaproanilide
  Colorless prism-like crystals (from methanol-water)
  Melting point: 93.5°–95.5° C.
p-Carboxy-α-chloroacetanilide
  Light yellow needle-like crystals (from ethanol-water)
  Melting point: 262.5°–264.0° C.

Reference Example 4

30 Grams of o-nitroaniline and 55.7 g of anhydrous chloroacetic acid were mixed together and the mixture was heated at 70° to 80° C. for 30 minutes with stirring, then water was added to the reaction mixture, the crystals thus formed were collected by filtration and recrystallized from isopropyl ether to obtain 49.42 g of o-nitro-α-chloroacetanilide in the form of light yellow flake-like crystals. Melting point: 85.5°–87.0° C.

By a method similar to the above, there were obtained compounds as follows:

o-Carbamoyl-α-chloroacetanilide
  Colorless needle-like crystals (from ethanol)
  Melting point: 187.5°–189.0° C.
p-Dimethylamino-α-chloroacetanilide
  Colorless needle-like crystals (from ethanol)

Melting point: 141°–142° C.
o-Acetyl-α-chloroacetanilide
 Colorless needle-like crystals (from isopropyl ether)
 Melting point: 78°–80.5° C. p1 m-Methylthio-α-chloroacetanilide
 Colorless needle-like crystals (from 70% water-containing methanol)
 Melting point: 105.5°–107.0° C.
o-Hydroxy-α-chloroacetanilide
 Colorless flake-like crystals (from 50% water-containing methanol)
 Melting point: 140.5–141.5° C.
o-Cyano-α-chloroacetanilide
 Colorless needle-like crystals (from 50% water-containing methanol)
 Melting point: 117.0°–119.0° C.
p-Sulfonamido-α-chloroacetanilide
 Colorless needle-like crystals (from methanol)
 Melting point: 220.0°–221.0° C.
m-Carbamoyl-α-chloroacetanilide
 Colorless needle-like crystals (from methanol)
 Melting point: 208.0°–209.5° C. (decomposed).
p-Carbamoyl-α-chloroacetanilide
 Colorless needle-like crystals (from 75% water-containing methanol)
 Melting point: 231.0°–233.0° C. (decomposed).
o-Hydroxy-m-nitro-α-chloroacetanilide
 Light yellow needle-like crystals (from methanol)
 Melting point: 243.0°–245.5° C. (decomposed).
o-Carbamoyl-α-bromobutyroanilide
 Colorless needle-like crystals (from methanol-water)
 Melting point: 143.5°–145.5° C.
o-Carbamoyl-γ-chlorobutyroanilide
 Colorless needle-like crystals (from methanol-water)
 Melting point: 112.5°–114.0° C.
o-Carbamoyl-ε-bromocaproanilide
 Colorless prism-like crystals (from methanol-water)
 Melting point: 93.5°–95.5° C.
o-Methoxycarbonyl-N-methyl-α-chloroacetanilide
 Colorless oily substance
 NMR(CDCl$_3$) δ: 3.21 (s, 3H), 3.73 (s, 2H), 3.87 (s, 3H), 7.23–7.73 (m, 3H), 7.98 (d-d, J=8 and 2 Hz).
p-Carboxy-α-chloroacetanilide
 Light yellow needle-like crystals (from ethanol-water)
 Melting point: 262.5°–264.0° C.

Reference Example 5

32 Grams of 4-(3,4-dimethoxybenzoyl)piperazine and 13.1 g of potassium hydroxide were dissolved in 300 ml of dimethylformamide (DMF), then under an ice-cooled condition with stirring, 10 g of α-chloroacetic acid was added thereto, next the reaction mixture was heated at 50° C. for 5 hours with stirring. After completion of the reaction, the reaction mixture was concentrated to dryness, the residue obtained was dissolved in water. The solution obtained was washed with chloroform, the aqueous layer was neutralized with concentrated hydrochloric acid, crystals formed were collected by filtration to obtain 9.8 g of α-[4-(3,4-dimethoxybenzoyl)-1-piperazinyl]acetic acid.

REFERENCE EXAMPLE 6

(a) 40 Grams of o-carbamoyl-α-chloroacetanilide, 40 g of benzylpiperazine, 52.4 ml of triethylamine and 250 ml of acetonitrile were heated at 50° C. for 5 hours with stirring, and crystals formed were collected by filtration. The crystals collected were extracted with chloroform and 1 N-sodium hydroxide aqueous solution, the chloroform layer was washed with water, dried then chloroform was removed by distillation. To the residue obtained was added ethanol and insoluble material formed was collected by filtration. Then the insoluble material was suspended in ethanol and was added hydrochloric acid/ethanol to make the pH of the mixture to about 1, then the solvent was removed by distillation. The residue obtained was crystallized by adding acetone, and recrystallized from methanol to obtain 54 g of o-carbamoyl-α-(4-benzyl-1-piperazinyl)acetanilide dihydrochloride. Colorless powdery crystals. Melting point: 218.5°–219.5° C. (decomposed).

(b) 50 Grams of o-carbamoyl-α-(4-benzyl-1-piperazinyl)acetanilide dihydrochloride, 4 g of 10%-palladium carbon, 70 ml of water and 300 ml of methanol were mixed together and the mixture was subjected to catalytic reduction at a room temperature. Then the catalyst was removed from the mother liquor, and the mother liquor was concentrated to dryness. The residue obtained was crystallized by adding acetone, and re-crystallized from water-acetone to obtain 35.2 g of o-carbamoyl-α-(1-piperazinyl)acetanilide dihydrochloride. Colorless cotton fiber-like crystals. Melting point: 239.5°–242° C. (decomposed).

EXAMPLE 1

6.5 Grams of o-methoxycarbonyl-α-(1-piperazinyl)acetanilide and 2.4 g of triethylamine were dissolved in 50 ml of methylene chloride, then a methylene chloride solution containing 5.4 g of 3,4-dimethoxybenzoyl chloride was added dropwise thereto under ice-cooled condition with stirring. The reaction was continued at the same temperature for 1 hour, then the reaction mixture was washed with water, 5%-sodium bicarbonate aqueous solution, next with potassium carbonate aqueous solution, and was dried. Methylene chloride was removed by distillation, the residue obtained was crystallized by adding ethyl acetate, the crystals formed were collected by filtration. Recrystallized from ethanol to obtain 7.5 g of o-methoxycarbonyl-α-[4-(3,4-dimethoxy-benzoyl)-1-piperazinyl]acetanilide in the form of colorless needle-like crystals. Melting point: 167.5°–169° C.

Elemental analysis (for C$_{23}$H$_{27}$O$_6$N$_3$) Calculated (%) C: 62.57; H: 6.16; N: 9.52; Found (%) C: 62.71; H: 6.10; N: 9.48.

EXAMPLE 2

3.3 Grams of p-methoxycarbonyl-α-(1-piperazinyl)acetanilide and 1.7 g of potassium carbonate were dissolved in 50 ml of DMF, then a methylene chloride solution containing 2.7 g of 3,4-dimethoxybenzoyl chloride was added dropwise thereto under ice-cooled condition with stirring. The reaction was continued at the same temperature for 2 hours, then to the reaction mixture was added 100 ml of methylene chloride, and the methylene chloride layer was washed with water, 5%-sodium bicarbonate aqueous solution, next with potassium carbonate aqueous solution, and was dried. Methylene chloride was removed by distillation, the residue obtained was purified by a silica gel column chromatography to obtain 3.3 g of p-methoxycarbonyl-α-[4-(3,4-dimethoxybenzoyl)-1-piperazinyl]acetanilide in the form of oily substance.

Elemental analysis (for $C_{23}H_{27}O_6N_3$) Calculated (%) C: 62.57; H: 6.16; N: 9.52; Found (%) C: 62.67; H: 6.05; N: 9.41.

NMR; $\delta_{ppm}^{CDCl_3}$=2.63 (m, 4H), 3.17 (s, 2H), 3.70 (m, 4H), 3.85 (s, 9H), 6.74–7.03 (m, 3H), 7.58 (d, J=8.5 Hz, 2H), 7.97 (d, J=8.5 Hz, 2H), 9.14 (br s, 1H)

The only substance was dissolved in isopropanol, and adjust the pH of the solution by adding hydrochloric acid-ethanol to about 1, and was crystallized from ether, then recrystallized from methanol to obtain p-methoxycarbonyl-α-[4-(3,4-dimethoxybenzoyl)-1-piperazinyl]acetanilide·monohydrochloride semihydrate in the form of colorless prism-like crystals. Melting point: 225.5°–227.5° C. (decomposed).

EXAMPLE 3

3.3 Grams of 3,4-dimethoxybenzoic acid was dissolved in 30 ml of dimethylformamide, then 2.4 g of triethylamine was added to this solution. Under ice-cooled condition, to this solution was added dropwise 2.75 g of isobutyl chloroformate with stirring, and further stirred for 30 minutes. Then to this reaction mixture was added dropwise a DMF solution containing 5.8 g of o-methoxycarbonyl-α-(1-piperazinyl)acetanilide and stirred for 5 hours. The reaction mixture was concentrated to dryness and subjected to extraction by adding chloroform and 1 N-sodium hydroxide. The chloroform layer was washed with water, dried and removed by distillation, the residue obtained was crystallized by adding ethyl acetate and the crystals formed were collected by filtration. Recrystallized from ethanol to obtain 2.3 g of o-methoxycarbonyl-α-[4-(3,4-dimethoxybenzoyl)-1-piperazinyl]acetanilide in the form of colorless needle-like crystals. Melting point: 167.5°–169.0° C.

EXAMPLE 4

By methods similar to those mentioned in Examples 1 and 3, there were obtained compounds as follows:

m-Methoxycarbonyl-α-[4-(3,4-dimethoxybenzoyl)-1-piperazinyl]acetanilide

Oily substance

NMR; $\delta_{ppm}^{CDCl_3}$=2.63 (m, 4H), 3.17 (s, 2H), 3.70 (m, 4H), 3.86 (s, 6H), 3.88 (s, 3H), 6.73–7.03 (m, 3H), 7.33–7.46 (m, 1H), 7.66–7.82 (m, 1H), 7.90–8.03 (m, 2H), 9.05 (s, 1H).

Monohydrochloride of the above-mentioned compound

Colorless needle-like crystals (from methanolisopropanol)

Melting point: 234°–235° C. (decomposed).

EXAMPLE 5

10.06 Grams of methyl o-(α-chloroacetylamino)benzoate, 15.2 g of N-(3,4-dimethoxybenzoyl)piperzine.-monohydrochloride and 16 g of triethylamine were suspended in 55 ml of acetonitrile, and the mixture was reacted at 49°–50° C. for 4 hours. After completion of the reaction, the reaction mixture was ice-cooled, and the crystals formed were collected by filtration. Recrystallized from ethanol to obtain 14.68 g of o-methoxycarbonyl-α-[4-(3,4-dimethoxybenzoyl)-1-piperazinyl]acetanilide in the form of colorless needle-like crystals. Melting point: 167.5°–169.0° C.

Elemental analysis (for $C_{23}H_{27}O_6N_3$) Calculated (%) C: 62.57; H: 6.16; N: 9.52; Found (%) C: 62.48; H: 6.15; N: 9.43.

EXAMPLE 6

5 Grams of methyl m-(α-chloroacetylamino)benzoate, 7.56 g of N-(3,4-dimethoxybenzoyl)piperazine monohydrochloride, 7.76 g of triethylamine and 30 ml of acetonitrile were mixed together and reacted at 45° to 50° C. for 5 hours. After completion of the reaction, the reaction mixture was ice-cooled, and the crystals formed were removed by filtration. The mother liquor was concentrated to dryness, and extracted by adding 1 N-sodium hydroxide aqueous solution and chloroform. The chloroform layer was washed with water, dried and removed by distillation. The oily substance obtained was purified by a silica gel column chromatography to obtain 10.08 g of m-methoxycarbonyl-α-[4-(3,4-dimethoxybenzoyl)-1-piperazinyl]acetanilide in the form of colorless oily substance.

Elemental analysis (for $C_{23}H_{27}O_6N_3$) Calculated (%) C: 62.57; H: 6.16; N: 9.52; Found (%) C: 62.42; H: 6.23; N: 9.61.

NMR; $\delta_{ppm}^{CDCl_3}$=2.63 (m, 4H), 3.17 (s, 2H), 3.70 (m, 4H), 3.86 (s, 6H), 3.88 (s, 3H), 6.73–7.03 (m, 3H), 7.33–7.46 (m, 1H), 7.66–7.82 (m, 1H), 7.90–8.03 (m, 2H), 9.05 (s, 1H)

By adding hydrochloric acid-ethanol, there was obtained m-methoxycarbonyl-α-[4-(3,4-dimethoxybenzoyl)-1-piperazinyl]acetanilide.monohydrochloride Colorless needle-like crystals (from methanolisopropanol)

Melting point: 234.0°–235.0° C. (decomposed).

EXAMPLE 7

By a method similar to that described in Example 5, there was obtained compound as follows: p-Methoxycarbonyl-α-[4-(3,4-dimethoxybenzoyl)-1-piperazinyl]acetanilide Colorless oily substance NMR; $\delta_{ppm}^{CDCl_3}$=2.63 (m, 4H), 3.17 (s, 2H), 3.70 (m, 4H), 3.85 (s, 9H), 6.74–7.03 (m, 3H), 7.58 (d, J=8.5 Hz, 2H), 7.97 (d, J=8.5 Hz, 2H), 9.14 (br s. 1H)

Monohydrochloride semihydrate of the above-mentioned compound

Colorless prism-like crystals (from methanol)

Melting point: 225.5°–227.5° C. (decomposed).

EXAMPLE 8

8.28 Grams of potassium carbonate was dissolved in 50 ml of water-acetone (1:2), and to this solution was added 15.1 g of o-methoxycarbonylaniline. Under ice-cooled condition, an acetone solution of 34.4 g of [4-(3,4-dimethoxybenzoyl)-1-piperazinyl]acetylchloride was added dropwise thereto. After completion of the addition, the reaction was carried out at a room temperature for 3 hours, then acetone was removed by distillation. The residue obtained was extracted with chloroform, then the extract was washed with water, dried and chloroform was removed by distillation. The residue obtained was crystallized by adding ethyl acetate, and the crystals were collected by filtration. Recrystallized from ethanol to obtain 29 g o-methoxycarbonyl-α-[4-3,4-dimethoxybenzoyl)-1-piperazinyl]acetanilide in the form of colorless needle-like crystals. Melting point: 167.5°–169.0° C.

EXAMPLE 9

2.5 Grams of [4-(4-methoxybenzoyl)-1-piperazinyl]acetic acid was dissolved in 30 ml of DMF, then 1.2 g of triethylamine was added thereto. Under an ice-cooled condition with stirring, 1.4 g of isobutyl chloroformate was added dropwise thereto and stirred for 30 minutes. Then, the reaction mixture was stirred at a room temperature, a DMF solution of 1.6 g of o-methoxycarbonylaniline was added dropwise to the reaction mixture and stirred for 6 hours. The reaction mixture obtained was concentrated to dryness, and the residue obtained was extracted with chloroform and 1 N-sodium hydroxide. The chloroform layer was washed with water, dried and then chloroform was removed by distillation. The residue obtained was crystallized by adding ethyl acetate, the crystals formed were collected by filtration. Recrystallized from ethanol to obtain 2.1 g of o-methoxycarbonyl-α-[4-(4-methoxybenzoyl)-1-piperazinyl]acetanilide in the form of colorless needle-like crystals. Melting point: 167.5°–169.0° C.

EXAMPLE 10

By methods similar to those described in Examples 8 and 9, there were obtained compounds as follows:

m-Methoxycarbonyl-α-[4-(3,4-dimethoxybenzoyl)-1-piperazinyl]acetanilide
Colorless oily substance
NMR; $\delta_{ppm}^{CDCl_3}$=2.63 (m, 4H), 3.17 (s, 2H), 3.70 (m, 4H), 3.86 (s, 6H), 3.88 (s, 3H), 6.73–7.03 (m, 3H), 7.33–7.46 (m, 1H), 7.66–7.82 (m, 1H), 7.90–8.03 (m, 2H), 9.05 (s, 1H).

Monohydrochloride of the above-mentioned compound
Colorless needle-like crystals (from methanolisopropanol)
Melting point: 234°–235° C. (decomposed).

p-Methoxycarbonyl-α-[4-(3,4-dimethoxybenzoyl)-1-piperazinyl]acetanilide
Colorless oily substance
NMR; $\delta_{ppm}^{CDCl_3}$=2.63 (m, 4H), 3.17 (s, 2H), 3.70 (m, 4H), 3.85 (s, 9H), 6.74–7.03 (m, 3H), 7.58 (d, J=8.5 Hz, 2H), 7.97 (d, J=8.5 Hz, 2H), 9.14 (br s, 1H).

Monohydrochloride semihydrate of the above-mentioned compound
Colorless prism-like crystals (from methanol)
Melting point: 225.5°–227.5° C. (decomposed).

EXAMPLE 11

5.00 Grams of o-carbamoyl-α-chloroacetanilide, 8.09 g of 3,4-dimethoxybenzoylpiperazine monohydrochloride, 8.31 g of triethylamine and 30 g of acetonitrile were mixed together and the mixture was stirred at 50° C. for 5 hours. Then the reaction mixture was ice-cooled, and the crystals formed were removed by filtration and the filtrate obtained was concentrated to dryness. The residue obtained was extracted with chloroform—1N sodium hydroxide aqueous solution, and the chloroform layer was washed with water, dried then chloroform was removed by distillation. The residue obtained was purified by a silica gel column chromatography and the desired product was converted into a hydrochloride by using hydrochloric acid-ethanol, then recrystallized from water-acetone to obtain 7.43 g of o-carbamoyl-α-[4-(3,4-dimethoxybenzoyl)-1-piperazinyl]acetanilide monohydrochloride monohydrate in the form of colorless needle-like crystals. Melting point: 122.0°–125.0° C. (decomposed).

By a method similar to the above, there were obtained compounds as follows:

o-Methoxycarbonyl-α-[4-(3,4-dimethoxybenzoyl)-1-piperazinyl]acetanilide monohydrochloride semihydrate
Colorless amorphous crystals (from ethanol-ether)
Melting point: 99°–101° C. (decomposed).

m-Methoxycarbonyl-α-[4-(3,4-dimethoxybenzoyl)-1-piperazinyl]acetanilide monohydrochloride
Colorless needle-like crystals (from methanolisopropanol)
Melting point: 234.0°–235.0° C. (decomposed).

p-Methoxycarbonyl-α-[4-(3,4-dimethoxybenzoyl)-1-piperazinyl]acetanilide monohydrochloride
Colorless prism-like crystals (from methanol)
Melting point: 225.5°–227.5° C. (decomposed).

o-Carboxy-α-[4-(3,4-dimethoxybenzoyl)-1-piperazinyl]acetanilide monohydrochloride
Colorless cotton fiber-like crystals (from 80% water-containing methanol)
Melting point: 250.5°–251.5° C. (decomposed).

o-Morpholinocarbonyl-α-[4-(3,4-dimethoxybenzoyl)-1-piperazinyl]acetanilide monohydrochloride
Colorless cotton fiber-like crystals (from ethanol)
Melting point: 201.5°–203.0° C. (decomposed).

o-Nitro-α-[4-(3,4-dimethoxybenzoyl)-1-piperazinyl]acetanilide monohydrochloride
Light yellow powdery crystals (from ethanol)
Melting point: 187.5°–188.5° C. (decomposed).

o-Amino-α-[4-(3,4-dimethoxybenzoyl)-1-piperazinyl]acetanilide dihydrochloride semihydrate
Colorless powdery crystals (from methanol)
Melting point: 204.0°–205.0° C. (decomposed).

o-Acetamido-α-[4-(3,4-dimethoxybenzoyl)-1-piperazinyl]acetanilide monooxalate
Colorless powdery crystals (from ethanol)
Melting point: 174.5°–176.0° C. (decomposed).

o-Acetyl-α-[4-(3,4-dimethoxybenzoyl)-1-piperazinyl]acetanilide
Colorless prism-like crystals (from ethanol)
Melting point: 153.5°–155.5° C.

o-Cyano-α-[4-(3,4-dimethoxybenzoyl)-1-piperazinyl]acetanilide monooxalate
Colorless powdery crystals (from methanol)
Melting point: 198.0°–199.5° C. (decomposed).

p-Dimethylamino-α-[4-(3,4-dimethoxybenzoyl)-1-piperazinyl]acetanilide dihydrochloride dihydrate
Colorless needle-like crystals (from ethanol)
Melting point: 159.0°–162.0° C. (decomposed).

m-Methylthio-α-[4-(3,4-dimethoxybenzoyl)-1-piperazinyl]acetanilide monohydrochloride
Colorless needle-like crystals (from ethanol)
Melting point: 188.5°–190.5° C.

p-Sulfonamido-α-[4-(3,4-dimethoxybenzoyl)-1-piperazinyl]acetanilide monohydrochloride
Colorless needle-like crystals (from methanol)
Melting point: 189.0°–192.0° C. (decomposed).

o-Hydroxy-α-[4-(3,4-dimethoxybenzoyl)-1-piperazinyl]acetanilide monohydrochloride
Colorless prism-like crystals (from ethanol)
Melting point: 209.0°–210.5° C. (decomposed).

m-Carbamoyl-α-[4-(3,4-dimethoxybenzoyl)-1-piperazinyl]acetanilide monooxalate
Colorless powdery crystals (from water-acetate)
Melting point: 206.5°–207° C. (decomposed).

p-Carbamoyl-α-[4-(3,4-dimethoxybenzoyl)-1-piperazinyl]acetanilide monohydrochloride monohydrate Colorless needle-like crystals (from water-acetone)
Melting point: 237.5°–239.0° C. (decomposed).

o-Hydroxy-m-nitro-α-[4-(3,4-dimethoxybenzoyl)-1-piperazinyl]acetanilide monohydrochloride ¾-hydrate
Yellow powdery crystals (from methanol-ether)
Melting point: 185.8°–188.0° C. (decomposed).

o-Carbamoyl-α-[4-(3,4-dimethoxybenzoyl)-1-piperazinyl]butyroanilide monooxalate
Colorless powdery crystals (from methanol-ether)
Melting point: 169°–170.5° C. (decomposed).

o-Carbamoyl-γ-[4-(3,4-dimethoxybenzoyl)-1-piperazinyl]butyroanilide monooxalate
Colorless powdery crystals (from water-acetone)
Melting point: 206°–206.5° C. (decomposed).

o-Carbamoyl-ε-[4-(3,4-dimethoxybenzoyl)-1-piperazinyl]carproanilide monooxalate
Colorless flake-like crystals (from ethanol)
Melting point: 130°–132° C. (decomposed).

o-Carbamoyl-α-[4-(3,4,5-trimethoxybenzoyl)-1-piperazinyl]acetanilide
Colorless prism-like crystals (from ethanol)
Melting point: 198.0°–199.5° C.

o-Carbamoyl-α-[4-(3-chlorobenzoyl)-1-piperazinyl]acetanilide monohydrochloride sesquihydrate
Colorless powdery crystals (from water)
Melting point: 158°–160° C.

o-Carbamoyl-α-[4-(4-nitrobenzoyl)-1-piperazinyl]acetanilide
Yellow needle-like crystals (from ethanol-water)
Melting point: 222.0°–224.0° C. (decomposed).

o-Methoxycarbonyl-N-methyl-α-[4-(3,4-dimethoxybenzoyl)-1-piperazinyl]acetanilide dioxalate
Colorless powdery crystals (from methanol-ether)
Melting point: 181.0°–182.0° C. (decomposed).

3,4,5-Trimethoxy-α-[4-(3,4-dimethoxybenzoyl)-1-piperazinyl]acetanilide monohydrochloride
Colorless needle-like crystals (from methanol)
Melting point: 234.0°–235.5° C. (decomposed).

o-Cyclohexylaminocarbonyl-α-[4-(3,4-dimethoxybenzoyl)-1-piperazinyl]acetanilide
Colorless prism-like crystals (from ethanol)
Melting point: 194.5°–196.0° C.

o-n-Butylaminocarbonyl-α-[4-(3,4-dimethoxybenzoyl)-1-piperazinyl]acetanilide monooxalate
Colorless powdery crystals (from ethanol-ether)
Melting point: 167°–168° C. (decomposed).

o-Diethylaminocarbonyl-α-[4-(3,4-dimethoxybenzoyl)-1-piperazinyl]acetanilide
Colorless granular crystals (from acetone)
Melting point: 106°–109° C.

o-Carbamoyl-α-[4-(4-methylbenzoyl)-1-piperazinyl]acetanilide
Colorless prism-like crystals (from ethanol)
Melting point: 182.5°–185.5° C.

o-Carbamoyl-α-[4-(4-cyanobenzoyl)-1-piperazinyl]acetanilide
Colorless flake-like crystals (from methanol)
Melting point: 213°–215.5° C.

p-Carboxy-α-[4-(3,4-dimethoxybenzoyl)-1-piperazinyl]acetanilide monohydrochloride sesquihydrate
Colorless needle-like crystals (from methanol)
Melting point: 170°–174° C.

EXAMPLE 12

6.15 Grams of o-carbamoyl-α-(1-piperazinyl)acetanilide and 2.4 g of triethylamine were dissolved in 50 ml of methylene chloride, then to this solution was added dropwise a methylene chloride solution of 5.4 g of 3,4-dimethoxybenzoyl chloride under ice-cooled condition with stirring. The reaction was carried out at the same temperature for 1 hour, then the reaction mixture was washed with water, 5%-sodium bicarbonate aqueous solution, and an aqueous solution of potassium carbonate, then dried. Methylene chloride was removed by distillation, the residue was purified by a silica gel column chromatography, the product obtained was converted into a hydrochloride by adding hydrochloric acid-ethanol, then recrystallized from water-acetone to obtain 5.1 g of o-carbamoyl-α-[4-(3,4-dimethoxybenzoyl)-1-piperazinyl]acetanilide monohydrochloride monohydrate in the form of colorless needle-like crystals. Melting point: 122.0°–125.0° C. (decomposed).

By a method similar to that described above, there were obtained compounds as follows:

o-Methoxycarbonyl-α-[4-(3,4-dimethoxybenzoyl)-1-piperazinyl]acetanilide monohydrochloride semihydrate
Colorless amorphous crystals (from ethanol-ether)
Melting point: 99°–101° C. (decomposed).

m-Methoxycarbonyl-α-[4-(3,4-dimethoxybenzoyl)-1-piperazinyl]acetanilide monohydrochloride
Colorless needle-like crystals (from methanolisopropanol)
Melting point: 234.0°–235.0° C. (decomposed).

p-Methoxycarbonyl-α-[4-(3,4-dimethoxybenzoyl)-1-piperazinyl]acetanilide monohydrochloride
Colorless prism-like crystals (from methanol)
Melting point: 225.5°–227.5° C. (decomposed).

o-Carboxy-α-[4-(3,4-dimethoxybenzoyl)-1-piperazinyl]acetanilide monohydrochloride
Colorless cotton fiber-like crystals (from 80% water-containing methanol)
Melting point: 250.5°–251.5° C. (decomposed).

o-Morpholinocarbonyl-α-[4-(3,4-dimethoxybenzoyl)-1-piperazinyl]acetanilide monohydrochloride
Colorless cotton fiber-like crystals (from ethanol)
Melting point: 201.5°–203.0° C. (decomposed).

o-Nitro-α-[4-(3,4-dimethoxybenzoyl)-1-piperazinyl]acetanilide monohydrochloride
Light yellow powdery crystals (from ethanol)
Melting point: 187.5°–188.5° C. (decomposed).

o-Amino-α-[4-(3,4-dimethoxybenzoyl)-1-piperazinyl]acetanilide dihydrochloride semihydrate
Colorless powdery crystals (from methanol)
Melting point: 204.0°–205.0° C. (decomposed).

o-Acetamido-α-[4-(3,4-dimethoxybenzoyl)-1-piperazinyl]acetanilide monooxalate
Colorless powdery crystals (from ethanol)
Melting point: 174.5°–176.0° C. (decomposed).

o-Acetyl-α-[4-(3,4-dimethoxybenzoyl)-1-piperazinyl]acetanilide
Colorless prism-like crystals (from ethanol)
Melting point: 153.5°–155.5° C.

o-Cyano-α-[4-(3,4-dimethoxybenzoyl)-1-piperazinyl]acetanilide monooxalate
Colorless powdery crystals (from methanol)
Melting point: 198.0°–199.5° C. (decomposed).

p-Dimethylamino-α-[4-(3,4-dimethoxybenzoyl)-1-piperazinyl]acetanilide dihydrochloride dihydrate
Colorless needle-like crystals (from ethanol)
Melting point: 159.0°–162.0° C. (decomposed).

m-Methylthio-α-[4-(3,4-dimethoxybenzoyl)-1-piperazinyl]acetanilide monohydrochloride
Colorless needle-like crystals (from ethanol)

Melting point: 188.5°–190.5° C.

p-Sulfonamido-α-[4-(3,4-dimethoxybenzoyl)-1-piperazinyl]acetanilide monohydrochloride
Colorless needle-like crystals (from methanol)
Melting point: 189.0°–192.0° C. (decomposed).

o-Hydroxy-α-[4-(3,4-dimethoxybenzoyl)-1-piperazinyl]acetanilide monohydrochloride
Colorless prism-like crystals (from ethanol)
Melting point: 209.0°–210.5° C. (decomposed).

m-Carbamoyl-α-[4-(3,4-dimethoxybenzoyl)-1-piperazinyl]acetanilide monooxalate
Colorless powdery crystals (from water-acetone)
Melting point: 206.5°–207° C. (decomposed).

p-Carbamoyl-α-[4-(3,4-dimethoxybenzoyl)-1-piperazinyl]acetanilide monohydrochloride monohydrate
Colorless needle-like crystals (from water-acetone)
Melting point: 237.5°–239.0° C. (decomposed).

o-Hydroxy-m-nitro-α-[4-(3,4-dimethoxybenzoyl)-1-piperazinyl]acetanilide monohydrochloride 3/4-hydrate
Yellow powdery crystals (from methanol-ether)
Melting point: 185.8°–188.0° C. (decomposed).

o-Carbamoyl-α-[4-(3,4-dimethoxybenzoyl)-1-piperazinyl]butyroanilide monooxalate
Colorless powdery crystals (from methanol-ether)
Melting point: 169°–170.5° C. (decomposed).

o-Carbamoyl-γ-[4-(3,4-dimethoxybenzoyl)-1-piperazinyl]butyroanilide monooxalate
Colorless powdery crystals (from water-acetone)
Melting point: 206°–206.5° C. (decomposed).

o-Carbamoyl-ε-[4-(3,4-dimethoxybenzoyl)-1-piperazinyl]caproanilide monooxalate
Colorless flake-like crystals (from ethanol)
Melting point: 130°–132° C. (decomposed).

o-Carbamoyl-α-[4-(3,4,5-trimethoxybenzoyl)-1-piperazinyl]acetanilide
Colorless prism-like crystals (from ethanol)
Melting point: 198.0°–199.5° C.

o-Carbamoyl-α-[4-(3-chlorobenzoyl)-1-piperazinyl]acetanilide monohydrochloride sesquihydrate
Colorless powdery crystals (from water)
Melting point: 158°–160° C.

o-Carbamoyl-α-[4-(4-nitrobenzoyl)-1-piperazinyl]acetanilide
Yellow needle-like crystals (from ethanol-water)
Melting point: 222.0°–224.0° C. (decomposed).

o-Methoxycarbonyl-N-methyl-α-[4-(3,4-dimethoxybenzoyl)-1-piperazinyl]acetanilide dioxalate
Colorless powdery crystals (from methanol-ether)
Melting point: 181.0°–182.0° C. (decomposed).

3,4,5-Trimethoxy-α-[4-(3,4-dimethoxybenzoyl)-1-piperazinyl]acetanilide monohydrochloride
Colorless needle-like crystals (from methanol)
Melting point: 234.0°–235.5° C. (decomposed).

o-Cyclohexylaminocarbonyl-α-[4-(3,4-dimethoxybenzoyl)-1-piperazinyl]acetanilide
Colorless prism-like crystals (from ethanol)
Melting point: 194.5°–196.0° C.

o-n-Butylaminocarbonyl-α-[4-(3,4-dimethoxybenzoyl)-1-piperazinyl]acetanilide monooxalate
Colorless powdery crystals (from ethanol-ether)
Melting point: 167°–168° C. (decomposed).

o-Diethylaminocarbonyl-α-[4-(3,4-dimethoxybenzoyl)-1-piperazinyl]acetanilide
Colorless granular crystals (from acetone)
Melting point: 106°–109° C.

o-Carbamoyl-α-[4-(4-methylbenzoyl)-1-piperazinyl]acetanilide
Colorless prism-like crystals (from ethanol)
Melting point: 182.5°–185.5° C.

o-Carbamoyl-α-[4-(4-cyanobenzoyl)-1-piperazinyl]acetanilide
Colorless flake-like crystals (from methanol)
Melting point: 213°–215.5° C.

p-Carboxy-α-[4-(3,4-dimethoxybenzoyl)-1-piperazinyl]acetanilide monohydrochloride sesquihydrate
Colorless needle-like crystals (from methanol)
Melting point: 170°–174° C.

EXAMPLE 13

3.3 Grams of 3,4-dimethoxybenzoic acid was dissolved in 30 ml of dimethylformamide, and to this solution was added 2.4 g of triethylamine. Under ice-cooled condition with stirring, 2.75 g of isobutyl chloroformate was added dropwise and the mixture obtained was stirred for 30 minutes. To this reaction mixture was added dropwise a dimethylformamide solution of 5.5 g of o-carbamoyl-α-(1-piperazinyl)acetanilide and was stirred for 5 hours. The reaction mixture was concentrated to dryness and extracted with chloroform-1N sodium hydroxide aqueous solution. The chloroform layer was washed with water, dried and chloroform was removed by distillation, the residue thus obtained was purified by a silica gel column chromatography and the product obtained was converted into a hydrochloride by adding hydrochloric acid-ethanol, recrystallized from water-acetone to obtain 1.5 g of o-carbamoyl-α-[4-(3,4-dimethoxybenzoyl)-1-piperazinyl]acetanilide monohydrochloride monohydrate in the form of colorless needle-like crystals. Melting point: 122.0°–125.0° C. (decomposed).

By a method similar to that described above, there were obtained compounds as follows:

o-Methoxycarbonyl-α-[4-(3,4-dimethoxybenzoyl)-1-piperazinyl]acetanilide monohydrochloride semihydrate
Colorless amorphous crystals (from ethanol-ether)
Melting point: 99°–101° C. (decomposed).

m-Methoxycarbonyl-α-[4-(3,4-dimethoxybenzoyl)-1-piperazinyl]acetanilide monohydrochloride
Colorless needle-like crystals (from methanolisopropanol)
Melting point: 234.0°–235.0° C. (decomposed).

p-Methoxycarbonyl-α-[4-(3,4-dimethoxybenzoyl)-1-piperazinyl]acetanilide monohydrochloride
Colorless prism-like crystals (from methanol)
Melting point: 225.5°–227.5° C. (decomposed).

o-Carboxy-α-[4-(3,4-dimethoxybenzoyl)-1-piperazinyl]-acetanilide monohydrochloride
Colorless cotton fiber-like crystals (from 80% water-containing methanol)
Melting point: 250.5°–251.5° C. (decomposed).

o-Morpholinocarbonyl-α-[4-(3,4-dimethoxybenzoyl)-1-piperazinyl]acetanilide monohydrochloride
Colorless cotton fiber-like crystals (from ethanol)
Melting point: 201.5°–203.0° C. (decomposed).

o-Nitro-α-[4-(3,4-dimethoxybenzoyl)-1-piperazinyl]acetanilide monohydrochloride
Light yellow powdery crystals (from ethanol)
Melting point: 187.5°–188.5° C. (decomposed).

o-Amino-α-[4-(3,4-dimethoxybenzoyl)-1-piperazinyl]acetanilide dihydrochloride semihydrate
Colorless powdery crystals (from methanol)

Melting point: 204.0°–205.0° C. (decomposed).

o-Acetamide-α-[4-(3,4-dimethoxybenzoyl)-1-piperazinyl]acetanilide monooxalate
Colorless powdery crystals (from ethanol)
Melting point: 174.5°–176.0° C. (decomposed).

o-Acetyl-α-[4-(3,4-dimethoxybenzoyl)-1-piperazinyl]acetanilide
Colorless prism-like crystals (from ethanol)
Melting point: 153.5°–155.5° C.

o-Cyano-α-[4-(3,4-dimethoxybenzoyl)-1-piperazinyl]acetanilide monooxalate
Colorless powdery crystals (from methanol)
Melting point: 198.0°–199.5° C. (decomposed).

p-Dimethylamino-α-[4-(3,4-dimethoxybenzoyl)-1-piperazinyl]acetanilide dihydrochloride dihydrate
Colorless needle-like crystals (from ethanol)
Melting point: 159.0°–162.0° C. (decomposed).

m-Methylthio-α-[4-(3,4-dimethoxybenzoyl)-1-piperazinyl]acetilide monohydrochloride
Colorless needle-like crystals (from ethanol)
Melting point: 188.5°–190.5° C.

p-Sulfonamido-α-[4-(3,4-dimethoxybenzoyl)-1-piperazinyl]acetanilide monohydrochloride
Colorless needle-like crystals (from methanol)
Melting point: 189.0°–192.0° C. (decomposed).

o-Hydroxy-α-[4-(3,4-dimethoxybenzoyl)-1-piperazinyl]acetanilide monohydrochloride
Colorless prism-like crystals (from ethanol)
Melting point: 209.0°–210.5° C. (decomposed).

m-Carbamoyl-α-[4-(3,4-dimethoxybenzoyl)-1-piperazinyl]acetanilide monooxalate
Colorless powdery crystals (from water-acetone)
Melting point: 206.5°–207° C. (decomposed).

p-Carbamoyl-α-[4-(3,4-dimethoxybenzoyl)-1-piperazinyl]acetanilide monohydrochloride monohydrate
Colorless needle-like crystals (from water-acetone)
Melting point: 237.5°–239.0° C. (decomposed).

o-Hydroxy-m-nitro-α-[4-(3,4-dimethoxybenzoyl)-1-piperazinyl]acetanilide monohydrochloride 3/4-hydrate
Yellow powdery crystals (from methanol-ether)
Melting point: 185.8°–188.0° C. (decomposed).

o-Carbamoyl-α-[4-(3,4-dimethoxybenzoyl)-1-piperazinyl]butyroanilide monooxalate
Colorless powdery crystals (from methanol-ether)
Melting point: 169°–170.5° C. (decomposed).

o-Carbamoyl-γ-[4-(3,4-dimethoxybenzoyl)-1-piperazinyl]butyroanilide monooxalate
Colorless powdery crystals (from water-acetone)
Melting point: 206°–206.5° C. (decomposed).

o-Carbamoyl-ε-[4-(3,4-dimethoxybenzoyl)-1-piperazinyl]caproanilide monooxalate
Colorless flake-like crystals (from ethanol)
Melting point: 130°–132° C. (decomposed).

o-Carbamoyl-α-[4-(3,4,5-trimethoxybenzoyl)-1-piperazinyl]acetanilide
Colorless prism-like crystals (from ethanol)
Melting point: 198.0°–199.5° C.

o-Carbamoyl-α-[4-(3-chlorobenzoyl)-1-piperazinyl]acetanilide monohydrochloride sesquihydrate
Colorless powdery crystals (from water)
Melting point: 158°–160° C.

o-Carbamoyl-α-[4-(4-nitrobenzoyl)-1-piperazinyl]acetanilide
Yellow needle-like crystals (from ethanol-water)
Melting point: 222.0°–224.0° C. (decomposed).

o-Methoxycarbonyl-N-methyl-α-[4-(3,4-dimethoxybenzoyl)-1-piperazinyl]acetanilide dioxalate
Colorless powder crystals (from methoanol-ether)
Melting point: 181.0°–182.0° C. (decomposed).

3,4,5-Trimethoxy-α-[4-(3,4-dimethoxybenzoyl)-1-piperazinyl]acetanilide monohydrochloride
Colorless needle-like crystals (from methanol)
Melting point: 234.0°–235.5° C. (decomposed).

o-Cyclohexylaminocarbonyl-α-[4-(3,4-dimethoxybenzoyl)-1-piperazinyl]acetanilide
Colorless prism-like crystals (from ethanol)
Melting point: 194.5°–196.0° C.

o-n-Butylaminocarbonyl-α-[4-(3,4-dimethoxybenzoyl)-1-piperazinyl]acetanilide monooxalate
Colorless powdery crystals (from ethanol-ether)
Melting point: 167°–168° C. (decomposed).

o-Diethylaminocarbonyl-α-[4-(3,4-dimethoxybenzoyl)-1-piperazinyl]acetanilide
Colorless granular crystals (from acetone)
Melting point: 106°–109° C.

o-Carbamoyl-α-[4-(4-methylbenzoyl)-1-piperazinyl]acetanilide
Colorless prism-like crystals (from ethanol)
Melting point: 182.5°–185.5° C.

o-Carbamoyl-α-[4-(4-cyanobenzoyl)-1-piperazinyl]acetanilide
Colorless flake-like crystals (from methanol)
Melting point: 213°–215.5° C.

p-Carboxy-α-[4-(3,4-dimethoxybenzoyl)-1-piperazinyl]acetanilide monohydrochloride sesquihydrate
Colorless needle-like crystals (from methanol)
Melting point: 170°–174° C.

EXAMPLE 14

8.28 Grams of potassium carbonate was dissolved in 50 ml of water-acetone (1:2), then 13.6 g of o-carbamoylaniline was added thereto. Under ice-cooled condition, an acetone solution of 34.4 g of [4-(3,4-dimethoxybenzoyl)-1-piperazinyl]acetyl chloride was added dropwise to the said mixture, then the reaction was carried out at a room temperature for 3 hours. Acetone was removed by distillation, the residue obtained was extracted with chloroform and the extract was washed with water, dried then chloroform was removed by distillation. The residue obtained was purified by a silica gel column chromatography, the product obtained was converted into a hydrochloride by adding hydrochloric acid-ethanol, recrystallized from water-acetone to obtain 16 g of o-carbamoyl-α-[4-(3,4-dimethoxybenzoyl)-1-piperazinyl]acetanilide monohydrochloride monohydrate in the form of colorless needle-like crystals. Melting point: 122.0°–125.0° C. (decomposed).

By a method similar to that described above, there were obtained compounds as follows:

o-Methoxycarbonyl-α-[4-(3,4-dimethoxybenzoyl)-1-piperazinyl]acetanilide monohydrochloride semihydrate
Colorless amorphous crystals (from ethanol-ether)
Melting point: 99°–101° C. (decomposed).

m-Methoxycarbonyl-α-[4-(3,4-dimethoxybenzoyl)-1-piperazinyl]acetanilide monohydrochloride
Colorless needle-like crystals (from methanolisopropanol)
Melting point: 234.0°–235.0° C. (decomposed).

p-Methoxycarbonyl-α-[4-(3,4-dimethoxybenzoyl)-1-piperazinyl]acetanilide monohydrochloride
Colorless prism-like crystals (from methanol)

Melting point: 225.5°–227.5° C. (decomposed).
o-Carboxy-α-[4-(3,4-dimethoxybenzoyl)-1-piperazinyl]acetanilide monohydrochloride
Colorless cotton fiber-like crystals (from 80% water-containing methanol)
Melting point: 250.5°–251.5° C. (decomposed).
o-Morpholinocarbonyl-α-[4-(3,4-dimethoxybenzoyl)-1-piperazinyl]acetanilide monohydrochloride
Colorless cotton fiber-like crystals (from ethanol)
Melting point: 201.5°–203.0° C. (decomposed).
o-Nitro-α-[4-(3,4-dimethoxybenzoyl)-1-piperazinyl]acetanilide monohydrochloride
Light yellow powdery crystals (from ethanol)
Melting point: 187.5°–188.5° C. (decomposed).
o-Amino-α-[4-(3,4-dimethoxybenzoyl)-1-piperazinyl]acetanilide dihydrochloride semihydrate
Colorless powdery crystals (from methanol)
Melting point: 204.0°–205.0° C. (decomposed).
o-Acetamido-α-[4-(3,4-dimethoxybenzoyl)-1-piperazinyl]acetanilide monooxalate
Colorless powdery crystals (from ethanol)
Melting point: 174.5°–176.0° C. (decomposed).
o-Acetyl-α-[4-(3,4-dimethoxybenzoyl)-1-piperazinyl]acetanilide
Colorless prism-like crystals (from ethanol)
Melting point: 153.5°–155.5° C.
o-Cyano-α-[4-(3,4-dimethoxybenzoyl)-1-piperazinyl]acetanilide monooxalate
Colorless powdery crystals (from methanol)
Melting point: 198.0°–199.5° C. (decomposed).
p-Dimethylamino-α-[4-(3,4-dimethoxybenzoyl)-1-piperazinyl]acetanilide dihydrochloride dihydrate
Colorless needle-like crystals (from ethanol)
Melting point: 159.0°–162.0° C. (decomposed).
m-Methylthio-α-[4-(3,4-dimethoxybenzoyl)-1-piperazinyl]acetanilide monohydrochloride
Colorless needle-like crystals (from ethanol)
Melting point: 188.5°–190.5° C.
p-Sulfonamido-α-[4-(3,4-dimethoxybenzoyl)-1-pirepazinyl]acetanilide monohydrochloride
Colorless needle-like crystals (from methanol)
Melting point: 189.0°–192.0° C. (decomposed).
o-Hydroxy-α-[4-(3,4-dimethoxybenzoyl)-1-piperazinyl]acetanilide monohydrochloride
Colorless prism-like crystals (from ethanol)
Melting point: 209.0°–210.5° C. (decomposed).
m-Carbamoyl-α-[4-(3,4-dimethoxybenzoyl)-1-piperazinyl]acetanilide monooxalate
Colorless powdery crystals (from water-acetone)
Melting point: 206.5°–207° C. (decomposed).
p-Carbamoyl-α-[4-(3,4-dimethoxybenzoyl)-1-piperazinyl]acetanilide monohydrochloride monohydrate
Colorless needle-like crystals (from water-acetone)
Melting point: 237.5°–239.0° C. (decomposed).
o-Hydroxy-m-nitro-α-[4-(3,4-dimethoxybenzoyl)-1-piperazinyl]acetanilide monohydrochloride 3/4-hydrate
Yellow powdery crystals (from methanol-ether)
Melting point: 185.8°–188.0° C. (decomposed).
o-Carbamoyl-α-[4-(3,4-dimethoxybenzoyl)-1-piperazinyl]butyroanilide monooxalate
Colorless powdery crystals (from methanol-water)
Melting point: 169°–170.5° C. (decomposed).
o-Carbamoyl-γ-[4-(3,4-dimethoxybenzoyl)-1-piperazinyl]butyroanilide monooxalate
Colorless powdery crystals (from water-acetone)
Melting point: 206°–206.5° C. (decomposed).
o-Carbamoyl-ε-[4-(3,4-dimethoxybenzoyl)-1-piperazinyl]caproanilide monooxalate
Colorless flake-like crystals (from ethanol)
Melting point: 130°–132° C. (decomposed).
o-Carbamoyl-α-[4-(3,4,5-trimethoxybenzoyl)-1-piperazinyl]acetanilide
Colorless prism-like crystals (from ethanol)
Melting point: 198.0°–199.5° C.
o-Carbamoyl-α-[4-(3-chlorobenzoyl)-1-piperazinyl]acetanilide monohydrochloride sesquihydrate
Colorless powdery crystal (from water)
Melting point: 158°–160° C.
o-Carbamoyl-α-[4-(4-nitrobenzoyl)-1-piperazinyl]acetanilide
Yellow needle-like crystals (from ethanol-water)
Melting point: 222.0°–224.0° C. (decomposed).
o-Methoxycarbony-N-methyl-α-[4-(3,4-dimethoxybenzoyl)-1-piperazinyl]acetanilide dioxalate
Colorless powdery crystals (from methanol-ether)
Melting point: 181.0°–182.0° C. (decomposed).
3,4,5-Trimethoxy-α-[4-(3,4-dimethoxybenzoyl)-1-piperazinyl]acetanilide monohydrochloride
Colorless needle-like crystals (from methanol)
Melting point: 234.0°–235.5° C. (decomposed).
o-Cyclohexylaminocarbonyl-α-[4-(3,4-dimethoxybenzoyl)-1-piperazinyl]acetanilide
Colorless prism-like crystals (from ethanol)
Melting point: 194.5°–196.0° C.
o-n-Butylaminocarbonyl-α-[4-(3,4-dimethoxybenzoyl)-1-piperazinyl]acetanilide monooxalate
Colorless powdery crystals (from ethanol-ether)
Melting point: 167°–168° C. (decomposed).
o-Diethylaminocarbonyl-α-[4-(3,4-dimethoxybenzoyl)-1-piperazinyl]acetanilide
Colorless granular crystals (from acetone)
Melting point: 106°–109° C.
o-Carbamoyl-α-[4-(4-methylbenzoyl)-1-piperazinyl]acetanilide
Colorless prism-like crystals (from ethanol)
Melting point: 182.5°–185.5° C.
o-Carbamoyl-α-[4-(4-cyanobenzoyl)-1-piperazinyl]acetanilide
Colorless flake-like crystals (from methanol)
Melting point: 213°–215.5° C.
p-Carboxy-α-[4-(3,4-dimethoxybenzoyl)-1-piperazinyl]acetanilide monohydrochloride sesquihydrate
Colorless needle-like crystals (from methanol)
Melting point: 170°–174° C.

EXAMPLE 15

2.77 Grams of [4-(3,4-dimethoxybenzoyl)-1-piperazinyl]-acetic acid was dissolved in 30 ml of DMF, then to this solution was added 1.2 g of triethylamine. Under ice-cooled condition with stirring, 1.4 g of isobutyl chloroformate was added dropwise thereto and stirred for 30 minutes. Further, the reaction mixture was stirred at a room temperature, a DMF solution of 1.46 g of o-carbamoylaniline was added dropwise to the mixture and was stirred for 6 hours. The reaction mixture obtained was concentrated to dryness, the residue was extracted with chloroform and 1N-sodium hydroxide aqueous solution. The chloroform layer was washed with water, dried then chloroform was removed by distillation. The residue obtained was purified by a silica gel column chromatography and the product obtained was converted into a hydrochloride by adding hydrochloric acid-ethanol, then recrystallized from water-acetone to obtain 0.7 g of o-carbamoyl-α-[4-(3,4-dimethoxybenzoyl)-1-piperazinyl]acetanilide monohydrochloride monohydrate in the form of colorless needle-like crystals. Melting point: 122.0°–125.0° C. (decomposed).

By a method similar to that described above, there were obtained compounds as follows:

o-Methoxycarbonyl-α-[4-(3,4-dimethoxybenzoyl]-piperazinyl]acetanilide monohydrochloride semihydrate
  Colorless amorphous crystals (from ethanol-ether)
  Melting point: 99°–101° C. (decomposed).
m-Methoxycarbonyl-α-[4-(3,4-dimethoxybenzoyl)-1-piperazinyl]acetanilide monohydrochloride
  Colorless needle-like crystals (from methanolisopropanol)
  Melting point: 234.0°–235.0° C. (decomposed).
p-Methoxycarbonyl-α-[4-(3,4-dimethoxybenzoyl)-1-piperazinyl]acetanilide monohydrochloride
  Colorless prism-like crystals (from methanol)
  Melting point: 225.5°–227.5° C. (decomposed).
o-Carboxy-α-[4-(3,4-dimethoxybenzoyl)-1-piperazinyl]acetanilide monohydrochloride
  Colorless cotton fiber-like crystals (from 80% water-containing methanol)
  Melting point: 250.5°–251.5° C. (decomposed).
o-Morpholinocarbonyl-α-[4-(3,4-dimethoxybenzoyl)-1-piperazinyl]acetanilide monohydrochloride
  Colorless cotton fiber-like crystals (from ethanol)
  Melting point: 201.5°–203.0° C. (decomposed).
o-Nitro-α-[4-(3,4-dimethoxybenzoyl)-1-piperazinyl]acetanilide monohydrochloride
  Light yellow powdery crystals (from ethanol)
  Melting point: 187.5°–188.5° C. (decomposed).
o-Amino-α-[4-(3,4-dimethoxybenzoyl)-1-piperazinyl]acetanilide dihydrochloride semihydrate
  Colorless powdery crystals (from methanol)
  Melting point: 204.0°–205.0° C. (decomposed).
o-Acetamido-α-[4-(3,4-dimethoxybenzoyl)-1-piperazinyl]acetanilide monooxalate
  Colorless powdery crystals (from ethanol)
  Melting point: 174.5–176.0° C. (decomposed).
o-Acetyl-α-[4-(3,4-dimethoxybenzoyl)-1-piperazinyl]acetanilide
  Colorless prism-like crystals (from ethanol)
  Melting point: 153.5°–155.5° C.
o-Cyano-α-[4-(3,4-dimethoxybenzoyl)-1-piperazinyl]acetanilide monooxalate
  Colorless powdery crystals (from methanol)
  Melting point: 198.0°–199.5° C. (decomposed).
p-Dimethylamino-α-[4-(3,4-dimethoxybenzoyl)-1-piperazinyl]acetanilide dihydrochloride dihydrate
  Colorless needle-like crystals (from ethanol)
  Melting point: 159.0°–162.0° C. (decomposed).
m-Methylthio-α-[4-(3,4-dimethoxybenzoyl)-1-piperazinyl]acetanilide monohydrochloride
  Colorless needle-like crystals (from ethanol)
  Melting point: 188.5°–190.5° C.
p-Sulfonamido-α-[4-(3,4-dimethoxybenzoyl)-1-pipera piperazinyl]acetanilide monohydrochloride
  Colorless needle-like crystals (from methanol)
  Melting point: 189.0°–192.0° C. (decomposed).
o-Hydroxy-α-[4-(3,4-dimethoxybenzoyl)-1-piperazinyl]acetanilide monohydrochloride
  Colorless prism-like crystals (from ethanol)
  Melting point: 209.0°–210.5° C. (decomposed).
m-Carbamoyl-α-[4-(3,4-dimethoxybenzoyl)-1-piperazinyl]acetanilide monooxalate
  Colorless powdery crystals (from water-acetone)
  Melting point: 206.5°–207° C. (decomposed).
p-Carbamoyl-α-[4-(3,4-dimethoxybenzoyl)-1-piperazinyl]-acetanilide monohydrochloride monohydrate
  Colorless needle-like crystals (from water-acetone)
  Melting point: 237.5°–239.0° C. (decomposed).
o-Hydroxy-m-nitro-α-[4-(3,4-dimethoxybenzoyl)-1-piperazinyl]acetanilide monohydrochloride 3/4-hydrate
  Yellow powdery crystals (from methanol-ether)
  Melting point: 185.8°–188.0° C. (decomposed).
o-Carbamoyl-α-[4-(3,4-dimethoxybenzoyl)-1-piperazinyl]butyroanilide monooxalate
  Colorless powdery crystals (from methanol-ether)
  Melting point: 169°–170.5° C. (decomposed).
o-Carbamoyl-γ-[4-(3,4-dimethoxybenzoyl)-1-piperazinyl]butyroanilide monooxalate
  Colorless powdery crystals (from water-acetone)
  Melting point: 206°–206.5° C. (decomposed).
o-Carbamoyl-ε-[4-(3,4-dimethoxybenzoyl)-1-piperazinyl]caproanilide monooxalate
  Colorless flake-like crystals (from ethanol)
  Melting point: 130°–132° C. (decomposed).
o-Carbamoyl-α-[4-(3,4,5-trimethoxybenzoyl)-1-piperazinyl]acetanilide
  Colorless prism-like crystals (from ethanol)
  Melting point: 198.0°–199.5° C.
o-carbamoyl-α-[4-(3-chlorobenzoyl)-1-piperazinyl]acetanilide monohydrochloride sesquihydrate
  Colorless powdery crystals (from water)
  Melting point: 158°–160° C.
o-Carbamoyl-α-[4-(4-nitrobenzoyl)-1-piperazinyl]acetanilide
  Yellow needle-like crystals (from ethanol-water)
  Melting point: 222.0°–224.0° C. (decomposed).
o-Methoxycarbonyl-N-methyl-α-[4-(3,4-dimethoxybenzoyl)-1-piperazinyl]acetanilide dioxalate
  Colorless powdery crystals (from methanol-ether)
  Melting point: 181.0°–182.0° C. (decomposed).
3,4,5-Trimethoxy-α-[4-(3,4-dimethoxybenzoyl)-1-piperazinyl]acetanilide monohydrochloride
  Colorless needle-like crystals (from methanol)
  Melting point: 234.0°–235.5° C. (decomposed).
o-Cyclohexylaminocarbonyl-α-[4-(3,4-dimethoxybenzoyl)-1-piperazinyl]acetanilide
  Colorless prism-like crystals (from ethanol)
  Melting point: 194.5°–196.0° C.
o-n-Butylaminocarbonyl-α-[4-(3,4-dimethoxybenzoyl)-1-piperazinyl]acetanilide monooxalate
  Colorless powdery crystals (from ethanol-ether)
  Melting point: 167°–168° C. (decomposed).
o-Diethylaminocarbonyl-α-[4-(3,4-dimethoxybenzoyl)-1-piperazinyl]acetanilide
  Colorless granular crystals (from acetone)
  Melting point: 106°–109° C.
o-Carbamoyl-α-[4-(4-methylbenzoyl)-1-piperazinyl]acetanilide
  Colorless prism-like crystals (from ethanol)
  Melting point: 182.5–185.5° C.
o-Carbamoyl-α-[4-(4-cyanobenzoyl)-1-piperazinyl]acetanilide
  Colorless flake-like crytals (from methanol)
  Melting point: 213°–215.5° C.
p-Carboxy-α-[4-(3,4-dimethoxybenzoyl)-1-piperazinyl]acetanilide monohydrochloride susquihydrate
  Colorless needle-like crystals (from methanol)

Melting point: 170°–174° c.

EXAMPLE 16

20 Grams of o-methoxycarbonyl- -[4-(3,4-dimethoxybenzoyl)-1-piperazinyl]acetanilide, 400 ml of methanol and 25 ml of 3.5N-potassium hydroxide methanol solution were mixed together and the mixture was refluxed for 8.5 hours. After completion of the reaction, the reaction mixture was allowed to stand for cooling, then an ethanol solution of hydrochloric acid was added to the mixture to adjust the pH thereof to about 1. The crystals formed were removed by filtration, and the mother liquor was cooled by ice. The crystals were collected by filtration, recrystallized from 80% water-containing methanol to obtain 13.28 g of o-carboxy- -[4-(3,4-dimethoxybenzoyl)-1-piperazinyl]acetanilide monohydrochloride in the form of colorless cotton fiber-like crystals. Melting point: 250.5°–251.5° C. (decomposed).

EXAMPLE 17

5 Grams of o-methoxycarbonyl- -[4-3,4-dimethoxybenzoyl)-1-piperazinyl]acetanilide was suspended in 50 ml of dimethylformamide, then 621 mg of 50% oily sodium hydride was added to the suspension and stirred at a room temperature for 1 hour. Next, under ice-cooled condition, 2.5 g of methyl iodide was added dropwise to the suspention and stirred at a room temperature for 4 hours. The solvent was removed by distillation under a reduced pressure, the residue obtained was extracted with chloroform and 1N-sodium hydroxide aqueous solution. The chloroform layer was washed with water, dried and then chloroform was removed by distillation. The residue obtained was purified by a silica gel column chromatography, and the product obtained was converted into an oxalate, recrystallized from methanol-ether to obtain 3.11 g of o-methoxy-carbonyl-N-methyl-α-[4-dimethoxy-benzoyl)-1-piperazinyl]-acetanilide dioxalate in the form of colorless powdery crystals. Melting point: 181.0°–182.0° C. (decomposed).

EXAMPLE 18

To 5 grams of o-carboxy-α-[4-(3,4-dimethoxybenzoyl)-1-piperazinyl]acetanilide hydrochloride was added 50 ml of dimethylformamide and 3.27 g of triethylamine, and the mixture obtained was cooled by ice with stirring, then 1.91 g of isobutyl chloroformate was added dropwise to the mixture, and the reaction was carried out at a room temperature for 1 hour. The reaction mixture was again cooled by ice with stirring, and 1.32 g of morpholine was added dropwise to the mixture then stirred at a room temperature for 3 hours. The reaction mixture was concentrated to dryness and extracted with 1N-sodium hydroxide aqueous solution and chloroform. The chloroform layer was washed with water, dried and chloroform was removed by distillation, the residue obtained was purified by a silica gel column chromatography. The oily substance obtained was dissolved in acetone and then the pH of this solution was adjusted to about pH 1 by adding an ethanol solution of hydrochloric acid, and the desired product was solidified (in the form of powder) by adding ether, Recrystallized from ethanol to obtain 860 mg of o-morpholinocarbonyl-α-[4-(3,4-dimethoxybenzoyl)-1-piperazinyl]acetanilide monohydrochloride in the form of cotton fiber-like crystals. Melting point: 201.5°–203.0° C. (decomposed).

EXAMPLE 19

10.53 Grams of 90% stannous chloride dihydrate was dissolved in 30 ml of concentrated hydrochloric acid, then 5 g of o-nitro-α-[4-(3,4-dimethoxybenzoyl)-1-piperazinyl]acetanilide was added thereto. The mixture obtained was stirred at a room temperature for 1 hour, then water and chloroform were added to the mixture, and under ice-cooling condition with stirring to 10N-sodium hydroxide aqueous solution was added thereto to adjust the pH to about 10–11. The chloroform layer was separated and washed with water, dried then chloroform was removed by distillation. The residue obtained was dissolved in ethanol and an ethanol solution of hydrochloric acid was added to this solution to make the pH thereof to about pH 1 to form crystals. The crystals precipitated were collected by filtration, recrystallized from methanol to obtain 2.73 g of o-amino-α-[4-(3,4-dimethoxybenzoyl)-1-piperazinyl]acetanilide dihydrochloride semihydrate in the form of colorless powdery crystals. Melting point: 204.0°–205.0° C. (decomposed).

Example of pharmaceutical preparation 1

By using a common procedure, tablets having the following formulations were prepared.

| | |
|---|---|
| α-[4-(3,4-Dimethoxybenzoyl)-1-piperazinyl]acetanilide monohydrochloride | 5 mg |
| Starch | 132 mg |
| Magnesium stearate | 18 mg |
| Lactose | 45 mg |
| Total | 200 mg |

Example of pharmaceutical preparation 2

| | |
|---|---|
| o-Methoxycarbonyl-α-[4-(3,4-dimethoxybenzoyl)-1-piperazinyl]acetanilide | 500 mg |
| Polyethylene glycol [Molecular weight: 4000] | 0.3 g |
| Sodium chloride | 0.9 g |
| Polyoxyethylene sorbitan monooleate | 0.4 g |
| Sodium metabisulfite | 0.1 g |
| Methyl p-hydroxybenzoate | 0.18 g |
| Propyl p-hydroxybenzoate | 0.02 g |
| Distilled water for injection | 100 ml |

Above prescribed methyl p-hydroxybenzoate, propyl p-hydroxybenzoate, sodium metabisulfite and sodium chloride were dissolved in distilled water at 80° C. under stirring. The solution obtained was cooled to 40° C., then compound of the present invention, polyethylene glycol and polyoxyethylene sorbitan monooleate were dissolved in this order in said solution. Then to this solution was added a sufficient amount of distilled water for injection so as to adjust the final regulated volume, sterilized by sterile filtration by using a suitable filter paper. One milliliter each of the solution obtained was filled in an ampoule separately to make injection preparations.

Example of pharmaceutical preparation 3

By using a common procedure, tablets having the following formulation were prepared.

| | |
|---|---|
| o-Carbamoyl-α-[4-(3,4-dimethoxy-benzoyl)-1-piperazinyl]acetanilide monohydrochloride monohydrate | 5 mg |
| Starch | 132 mg |
| Magnesium stearate | 18 mg |
| Lactose | 45 mg |
| Total | 200 mg |

What is claimed is:

1. An aniline derivative and its pharmaceutically acceptable salts having the formula,

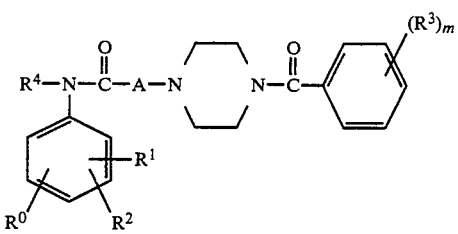

wherein $R^0$, $R^1$ and $R^2$ are the same or different and each is selected from the group consisting of a hydrogen atom, a halogen atom, a nitro group, an amino group, a carboxy group, a cyano group, a hydroxy group, a sulfonamido group, a lower alkyl group, a lower alkoxycarbonyl group, a lower alkoxy group, a lower alkanoyl group, a lower alkylamino group, a lower alkylthio group, a lower alkanoylamino group or a group of the formula

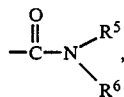

wherein $R^5$ and $R^6$ are the same or different and each is selected from the group consisting of a hydrogen atom, a lower alkyl group or a $C_3$ to $C_8$ cycloalkyl group or together with the N atom adjacent thereto form a morpholino group; $R^3$ is a cyano group, a nitro group, a halogen atom, a lower alkyl group or a lower alkoxy group; m is an interger of 1 to 3; $R^4$ is a hydrogen atom or a lower alkyl group; and A is a lower alkylene group; provided that when $R^3$ is a lower alkoxy group, a halogen atom or a lower alkyl group; and when $R^0$ is a hydrogen atom and A is a methylene group, then $R^1$ and $R^2$ are the same or different and should not be hydrogen atoms, halogen atoms, lower alkyl groups or lower alkoxy groups; further that when $R^3$ is a lower alkoxy group, a halogen atom or a lower alkyl group, and $R^0$ is a halogen atom, a lower alkyl group or a lower alkoxy group and A is a methylene group, then either one of $R^1$ and $R^2$ is a hydrogen atom and the other one should not be a halogen atom, a lower alkyl group or a lower alkoxy group.

2. The aniline derivative of claim 1, wherein $R^0$, $R^1$ and $R^2$ are the same or different and each is selected from the group consisting of a hydrogen atom, a nitro group, an amino group, a carboxy group, a cyano group, a hydroxy group, a sulfonamido group, a lower alkoxycarbonyl group, a lower alkanoyl group, a lower alkylamino group, a lower alkylthio group, a lower alkanoylamino group or a group of the formula

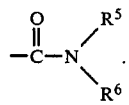

3. The aniline derivative of claim 2, wherein $R^0$ and $R^1$ are hydrogen atoms and $R^2$ is a nitro group, a cyano group, a carboxy group, a lower alkoxycarbonyl group, or a group of the formula

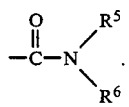

4. The aniline derivative of claim 3, wherein $R^2$ is a lower alkoxycarbonyl group.

5. The aniline derivative of claim 2, wherein $R^0$ and $R^1$ are hydrogen atoms and $R^2$ is an amino group, a hydroxy group, a sulfonamido group, a lower alkanoyl group, a lower alkylamino group, a lower alkylthio group or a lower alkanoylamino group.

6. The aniline derivative of any one of claims 3, 4 or 5, wherein $R^3$ is a lower alkoxy group.

7. o-Methoxycarbonyl-α-[4-(3,4-dimethoxybenzoyl)-1-piperazinyl]acetanilide.

8. o-Cyano-α-[4-(3,4-dimethoxybenzoyl)-1-piperazinyl]acetanilide.

9. o-Nitro-α-[4-(3,4-dimethoxybenzoyl)-1-piperazinyl]acetanilide.

10. o-Carbamoyl-α-[4-(3,4-dimethoxybenzoyl)-1-piperazinyl]acetanilide.

11. m-Methoxycarbonyl-α-[4-(3,4-dimethoxybenzoyl)-1-piperazinyl]acetanilide.

12. p-Methoxycarbonyl-α-[4-(3,4-dimethoxybenzoyl)-1-piperazinyl]acetanilide.

13. A cardiotonic composition containing an effective amount of an aniline derivative of claim 1 as the active ingredient in combination with a pharmaceutically acceptable carrier.

* * * * *